(12) United States Patent
Gilman et al.

(10) Patent No.: US 6,306,649 B1
(45) Date of Patent: *Oct. 23, 2001

(54) HETEROLOGOUS TRANSCRIPTION FACTORS

(75) Inventors: Michael Z. Gilman, Newton; Sridaran Natesan, Chestnut Hill, both of MA (US)

(73) Assignee: ARIAD Gene Therapeutics, Inc., Cambridge, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/672,213

(22) Filed: Jun. 27, 1996

Related U.S. Application Data

(60) Provisional application No. 60/019,614, filed on Dec. 29, 1995, and provisional application No. 60/000,553, filed on Jun. 27, 1995.

(51) Int. Cl.$^7$ .............................. C12N 5/00; C12N 15/63; C12N 15/00; C12N 15/09

(52) U.S. Cl. .................. 435/325; 435/320.1; 435/455; 435/69.1; 574/44; 536/23.1; 536/23.4; 536/23.5

(58) Field of Search ................... 435/6, 69.1, 91.1, 435/172.1, 172.3, 325, 375, 377, 366, 320.1, 455; 800/2, DIG. 1, DIG. 2; 514/44; 424/199.1, 93.21; 536/23.1, 23.4, 23.5

(56) References Cited

U.S. PATENT DOCUMENTS

| | | | |
|---|---|---|---|
| 5,082,670 | * 1/1992 | Gage et al. | 424/520 |
| 5,262,300 | * 11/1993 | Evans et al. | 435/6 |
| 5,534,418 | * 7/1996 | Evans et al. | 435/69.1 |
| 5,597,693 | * 1/1997 | Evans et al. | 435/6 |
| 5,830,462 | 11/1998 | Crabtree et al. | 424/93.21 |

FOREIGN PATENT DOCUMENTS

| | | |
|---|---|---|
| WO 96/41865 | 12/1996 | (WO) . |
| WO 97/12040 | 4/1997 | (WO) . |

OTHER PUBLICATIONS

Orkin et al., Report and Recomendations of the Panel to Assess the NIH Investment in Research on Gene Therapy, 1995.*

Eck and Wilson, Goodman & Gilman's The Pharmacological Basis of Therapeutics, McGraw–Hill: New York, Ninth Edition, 1995.*

Orloff et al., Nature, vol. 347, pp. 189–190, 1990.*

Lui et al., Immunology Today, vol. 14(6), pp. 290–295, 1993.*

Weintraub et al., Science, vol. 251, pp. 761–766, 1991.*

Bergmann et al., J. Steroid Biochem. Molec. Biol., vol. 49(2/3), pp. 139–152, 1994.*

Qi et al., Molecular and Cellular Biology, vol. 5(3), pp. 1817–1825 1995.*

Sadowski et al., Nature, vol. 362, pp. 79–83, 1993.*

M. Schmitz et al. EMBO J. 10(12) 3805–17, 1991.*

R. Selden et al. Science 236: 714–8, 1987.*

G. Fishman et al. J. Clin. Invent. 93: 1864–8, 1994.*

Oligino et al., Gene Therapy, vol. 8, pp. 892–899, 1996.*

Veelken et al., Int. J. Mol. Med., vol. 2, No. 4, pp. 423–428, 1998.*

Ruben et al., (1992) Mol Cell Biol 12:444–454.

Blair et al., (1994) Mol Cell Biol 14:7226–7234.

Emami and Carey (1992) EMBO J. 11:5005–5012.

Kodadek and Johnston (1995) Chemistry and Biology 2:187–194.

Paal, K., Nucleic Acids Research, 25(5): 1050–1055 (1997).

Lin, Y.–S. et al., Cell, 54: 659–664 (1988).

Schmitz, M. et al., J. Biol. Chem., 270: 15576–15584 (1995).

Hollenberg, M. and Evans, R.,, Cell, 55: 889–906 (1988).

Tate, B. et al., FASEB J., 10: 1524–1531, (1996).

Sauer, F., Science 270: 1783–1788, (1995).

White et al., (1992) EMBO J. Jun;11(6):2229–40.

Sublett et al., (1995) Oncogene. Aug 3;11(3):545–52.

Le Douarin et al., (1995) Nucleic Acids Research 23:876–878.

* cited by examiner

*Primary Examiner*—Jill D. Martin
(74) *Attorney, Agent, or Firm*—David L. Berstein

(57) ABSTRACT

This invention provides novel materials and methods involving the heterologous expression of transcription factors which are useful for effecting transcription of target genes in genetically engineered cells or organisms containing them. Target gene constructs and other materials useful for practicing the invention are also disclosed.

2 Claims, 7 Drawing Sheets

SEQUENCE LISTING (1) GENERAL INFORMATION:

(iii) NUMBER OF SEQUENCES: 72

(2) INFORMATION FOR SEQ ID NO:1:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Asp Phe Asp Leu Asp Met Leu Gly
1               5

(2) INFORMATION FOR SEQ ID NO:2:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Asp Phe Asp Leu Asp Met Leu Gly Gly
1               5

(2) INFORMATION FOR SEQ ID NO:3:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

TAATTANGGG NG                                                             12

(2) INFORMATION FOR SEQ ID NO:4:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Asn Phe Leu Gln Leu Pro Gln Gln Thr Gln Gly Ala Leu Leu Thr Ser
1               5                   10                  15

Gln Pro (2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO:5:

Ser Tyr Gly Gln Gln Ser
1               5

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

ATGCTCTAGA GAACGCCCAT ATGCTTGCCC T                                    31

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

ATGCGCGGCC GCCGCCTGTG TGGGTGCGGA TGTG                                 34

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

ATGCGCGGCC GCAGGAGGAA GAAACGCACC AGC                                  33

(2) INFORMATION FOR SEQ ID NO:9:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GCATGGATCC GATTCAACTA GTGTTGATTC TTTTTTCTTT CTGGCGGCG                 49

(2) INFORMATION FOR SEQ ID NO:10:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
CTGGGGGCCT TGCTTGGCAA CAGCACAGAC CCAGCTGTGT TCACAGACCT GGCATCCGTC      60

GACAACTCCG AGTTTCAGCA GCTGCTGAAC CAGGGCATAC CTGTGGCCCC CCACACAACT     120

GAGCCCATGC TGATGGAGTA CCCTGAGGCT ATAACTCGCC TAGTGACAGG GGCCCAGAGG     180

CCCCCCGACC CAGCTCCTGC TCCACTGGGG GCCCCGGGGC TCCCCAATGG CCTCCTTTCA     240

GGAGATGAAG ACTTCTCCTC CATTGCGGAC ATGGACTTCT CAGCCCTGCT GAGTCAGATC     300

AGCTCC                                                                306
```

(2) INFORMATION FOR SEQ ID NO:11:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
GATGAGTTTC CCACCATGGT GTTTCCTTCT GGGCAGATCA GCCAGGCCTC GGCCTTGGCC      60

CCGGCCCCTC CCCAAGTCCT GCCCCAGGCT CCAGCCCCTG CCCCTGCTCC AGCCATGGTA     120

TCAGCTCTGG CCCAGGCCCC AGCCCCTGTC CCAGTCCTAG CCCCAGGCCC TCCTCAGGCT     180

GTGGCCCCAC CTGCCCCCAA GCCCACCCAG GCTGGGGAAG GAACGCTGTC AGAGGCCCTG     240

CTGCAGCTGC AGTTTGATGA TGAAGACCTG GGGGCCTTGC TTGGCAACAG CACAGACCCA     300

GCTGTGTTCA CAGACCTGGC ATCCGTCGAC AACTCCGAGT TCAGCAGCT GCTGAACCAG      360

GGCATACCTG TGGCCCCCCA CACAACTGAG CCCATGCTGA TGGAGTACCC TGAGGCTATA     420

ACTCGCCTAG TGACAGCCCA GAGGCCCCCC GACCCAGCTC CTGCTCCACT GGGGGCCCCG     480

GGGCTCCCCA ATGGCCTCCT TTCAGGAGAT GAAGACTTCT CCTCCATTGC GGACATGGAC     540

TTCTCAGCCC TGCTGAGTCA GATCAGCTCC TAA                                 573
```

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
GCATGTCTAG AGAGATGTGG CATGAAGGCC TGGAAG                                36
```

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
GCATCACTAG TCTTTGAGAT TCGTCGGAAC ACATG                                 35
```

```
(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GCACATTCTA GAATTGATAC GCCCAGACCC TTG                                  33

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CGATCAACTA GTAAGTGTCA ATTTCCGGGG CCT                                  33

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GCACTATCTA GACTGAAGAA CATGTGTGAG CACAGC                               36

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GCACTATCTA GAGTGAGCGA GGAGCTGATC CGAGTG                               36

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

CGATCAACTA GTGGAAACAT ATTGCAGCTC TAAGGA                               36

(2) INFORMATION FOR SEQ ID NO:19:

(i) SEQUENCE CHARACTERISTICS:
        (A) LENGTH: 36 base pairs
```

(B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CGATCAACTA GTTGGCACAG CCAATTCAAG GTCCCG                                    36

(2) INFORMATION FOR SEQ ID NO:20:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

ATGCTCTAGA CTGGGGGCCT TGCTTGGCAA C                                         31

(2) INFORMATION FOR SEQ ID NO:21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

ATGCTCTAGA GATGAGTTTC CCACCATGGT G                                         31

(2) INFORMATION FOR SEQ ID NO:22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

GCATGGATCC GCTCAACTAG TGGAGCTGAT CTGACTCAG                                 39

(2) INFORMATION FOR SEQ ID NO:23:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

ATGCTCTAGA CTTGGAACCG GACCTGCCGC C                                         31

(2) INFORMATION FOR SEQ ID NO:24:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

GCATCACTAG TCCAGAAAGG GCACCAGCCA ATAT                          34

(2) INFORMATION FOR SEQ ID NO:25:

(i) SEQUENCE CHARACTERISTICS:
            (A) LENGTH: 6 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:25:

TCTAGA                                                         6

(2) INFORMATION FOR SEQ ID NO:26:

(i) SEQUENCE CHARACTERISTICS:
            (A) LENGTH: 6 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:26:

ACGAGT                                                         6

(2) INFORMATION FOR SEQ ID NO:27:

(i) SEQUENCE CHARACTERISTICS:
            (A) LENGTH: 6 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:27:

GGATCC                                                         6

(2) INFORMATION FOR SEQ ID NO:28:

(i) SEQUENCE CHARACTERISTICS:
            (A) LENGTH: 134 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 13..133

(xi) SEQUENCE DESCRIPTION: SEQ ID NO:28:

GTAGAAGCGC GT ATG GCT TCT AGC TAT CCT TAT GAC GTG CCT GAC TAT         48
              Met Ala Ser Ser Tyr Pro Tyr Asp Val Pro Asp Tyr
               1               5                  10

GCC AGC CTG GGA GGA CCT TCT AGT CCT AAG AAG AAG AGA AAG GTG TCT       96
Ala Ser Leu Gly Gly Pro Ser Ser Pro Lys Lys Lys Arg Lys Val Ser
             15                  20                  25

AGA GAA CGC CCA TAT GCT TGC CCT GTC GAG TCC TGC   G A                134
Arg Glu Arg Pro Tyr Ala Cys Pro Val Glu Ser Cys
     30                  35                  40

(2) INFORMATION FOR SEQ ID NO:29:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO:29:

```
Met Ala Ser Ser Tyr Pro Tyr Asp Val Pro Asp Tyr Ala Ser Leu Gly
 1               5                  10                  15
Gly Pro Ser Ser Pro Lys Lys Lys Arg Lys Val Ser Arg Glu Arg Pro
             20                  25                  30
Tyr Ala Cys Pro Val Glu Ser Cys
             35                  40
```

(2) INFORMATION FOR SEQ ID NO:30:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..40

(xi) SEQUENCE DESCRIPTION: SEQ ID NO:30:

```
AGA ATC AAC ACT AGA GAG ATG TGG CAT GAA GGC CTG GAA  G A          41
Arg Ile Asn Thr Arg Glu Met Trp His Glu Gly Leu Glu
                 45                  50
```

(2) INFORMATION FOR SEQ ID NO:31:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO:31:

```
Arg Ile Asn Thr Arg Glu Met Trp His Glu Gly Leu Glu
 1               5                  10
```

(2) INFORMATION FOR SEQ ID NO:32:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..25

(xi) SEQUENCE DESCRIPTION: SEQ ID NO:32:

```
CGA ATC TCA AAG ACT AGT TAT TAG  G GATCCTGAG           34
Arg Ile Ser Lys Thr Ser Tyr  *
 15                  20
```

(2) INFORMATION FOR SEQ ID NO:33:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:33:

```
Arg Ile Ser Lys Thr Ser Tyr
 1               5
```

(2) INFORMATION FOR SEQ ID NO:34:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

```
GAATTCCTAG AAGCGACCAT GGCTTCTAGC                              30
```

(2) INFORMATION FOR SEQ ID NO:35:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

```
GAAGAGAAAG GTGGCTAGCG AACGCCCATA T                            31
```

(2) INFORMATION FOR SEQ ID NO:36:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

```
GCCATGGTGG CTAGCCTATA GTGAG                                   25
```

(2) INFORMATION FOR SEQ ID NO:37:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

```
GGCGGTGTTG GCTAGCGTCG GTCAG                                   25
```

(2) INFORMATION FOR SEQ ID NO:38:

(i) SEQUENCE CHARACTERISTICS:

(A) LENGTH: 123 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 18..98

(xi) SEQUENCE DESCRIPTION: SEQ ID NO:38:

```
GAATTCCAGA AGCGCGT ATG GCT TCT AGC TAT CCT TAT GAC GTG CCT GAC         50
                   Met Ala Ser Ser Tyr Pro Tyr Asp Val Pro Asp
                     10                      15

TAT GCC AGC CTG GGA GGA CCT TCT AGT CCT AAG AAG AAG AGA AAG GTG        98
Tyr Ala Ser Leu Gly Gly Pro Ser Ser Pro Lys Lys Lys Arg Lys Val
 20              25                  30                  35

TCTAGATATC GAGGATCCCA AGCTT                                           123
```

(2) INFORMATION FOR SEQ ID NO:39:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:39:

```
Met Ala Ser Ser Tyr Pro Tyr Asp Val Pro Asp Tyr Ala Ser Leu Gly
 1               5                  10                  15

Gly Pro Ser Ser Pro Lys Lys Lys Arg Lys Val
             20                  25
```

(2) INFORMATION FOR SEQ ID NO:40:

(i) SEQUENCE CHARACTERISTICS:
        (A) LENGTH: 222 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

```
GCTAGCTAAT GATGGGCGCT CGAGTAATGA TGGGCGGTCG ACTAATGATG GGCGCTCGAG        60

TAATGATGGG CGTCTAGCTA ATGATGGGCG CTCGAGTAAT GATGGGCGGT CGACTAATGA       120

TGGGCGCTCG AGTAATGATG GGCGTCTAGC TAATGATGGG CGCTCGAGTA ATGATGGGCG       180

GTCGACTAAT GATGGGCGCT CGAGTAATGA TGGGCGTCTA GA                          222
```

(2) INFORMATION FOR SEQ ID NO:41:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

```
TCTAGAACGC GAATTCCGGT AGGCGTGTAC GGTGGGAGGT CTATATAAGC AGAGCTCGTT        60

TAGTGAACCG TCAGATCGCC TGGAGACGCC ATCCACGCTG TTTTGACCTC CATAGAAGCT       120
```

T                                                                            121

(2) INFORMATION FOR SEQ ID NO:42:

(i) SEQUENCE CHARACTERISTICS:
        (A) LENGTH: 141 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

TCTAGAACGC GAATTCAACA TTTTGACACC CCCATAATAT TTTTCCAGAA TTAACAGTAT      60

AAATTGCATC TCTTGTTCAA GAGTTCCCTA TCACTCTCTT TAATCACTAC TCACAGTAAC     120

CTCAACTCCT GCCACAAGCT T                                               141

(2) INFORMATION FOR SEQ ID NO:43:

(i) SEQUENCE CHARACTERISTICS:
        (A) LENGTH: 304 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

ATCGATGTTT TCTGAGTTAC TTTTGTATCC CCACCCCCCC TCGAGCTTGC ATGCCTGCAG      60

GTCGGAGTAC TGTCCTCCGA GCGGAGTACT GTCCTCCGAG CGGAGTACTG TCCTCCGAGC     120

GGAGTACTGT CCTCCGAGCG GAGTACTGTC CTCCGAGCGC AGACTCTAGA GGATCCGAGA     180

ACATTTTGAC ACCCCCATAA TATTTTTCCA GAATTAACAG TATAAATTGC ATCTCTTGTT     240

CAAGAGTTCC CTATCACTCT CTTTAATCAC TACTCACAGT AACCTCAACT CCTGCCACAA     300

GCTT                                                                  304

(2) INFORMATION FOR SEQ ID NO:44:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

CCCGTGGTCC CGCGTTGCTT CGAT                                             24

(2) INFORMATION FOR SEQ ID NO:45:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

CTGGGGGCCT TGCTTGGCAA CAGCACAGAC CCAGCTGTGT TCACAGACCT GGCATCCGTC      60

GACAACTCCG AGTTTCAGCA GCTGCTGAAC CAGGGCATAC CTGTGGCCCC CCACACAACT     120

GAGCCCATGC TGATGGAGTA CCCTGAGGCT ATAACTCGCC TAGTGACAGG GGCCCAGAGG     180

```
CCCCCCGACC CAGCTCCTGC TCCACTGGGG GCCCCGGGGC TCCCCAATGG CCTCCTTTCA      240

GGAGATGAAG ACTTCTCCTC CATTGCGGAC ATGGACTTCT CAGCCCTGCT GAGTCAGATC      300

AGCTCC                                                                306
```

(2) INFORMATION FOR SEQ ID NO:46:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

```
CTAGCTAATG ATGGGCGCTC GAGTAATGAT GGGCGGTCGA CTAATGATGG GCGCTCGAGT       60

AATGATGGGC GT                                                           72
```

(2) INFORMATION FOR SEQ ID NO:47:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

```
ATGCTCTAGA GAACGCCCAT ATGCTTGCCC T                                      31
```

(2) INFORMATION FOR SEQ ID NO:48:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

```
ATGCGCGGCC GCCGCCTGTG TGGGTGCGGA TGTG                                   34
```

(2) INFORMATION FOR SEQ ID NO:49:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

```
ATGCGCGGCC GCAGGAGGAA GAAACGCACC AGC                                    33
```

(2) INFORMATION FOR SEQ ID NO:50:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

GCATGGATCC GATTCAACTA GTGTTGATTC TTTTTTCTTT CTGGCGGCG  49

(2) INFORMATION FOR SEQ ID NO:51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:51:

TCAGTCTAGA GGAGTGCAGG TGGAAACCAT  30

(2) INFORMATION FOR SEQ ID NO:52:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

TCAGGGATCC TCAATAACTA GTTTCCAGTT TTAGAAGCTC  40

(2) INFORMATION FOR SEQ ID NO:53:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

ACTGTCTAGA GTCAGCCTGG GGGACGAG  28

(2) INFORMATION FOR SEQ ID NO:54:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:54:

GCATGGATCC GATTCAACTA GTCCCACCGT ACTCGTCAAT TCC  43

(2) INFORMATION FOR SEQ ID NO:55:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

ATGCTCTAGA CTGGGGGCCT TGCTTGGCAA C  31

(2) INFORMATION FOR SEQ ID NO:56:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

GCATGGATCC GCTCAACTAG TGGAGCTGAT CTGACTCAG                    39

(2) INFORMATION FOR SEQ ID NO:57:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

ATGCTCTAGA GATGAGTTTC CCACCATGGT G                            31

(2) INFORMATION FOR SEQ ID NO:58:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

GCATGGATCC GCTCAACTAG TGGAGCTGAT CTGACTCAG                    39

(2) INFORMATION FOR SEQ ID NO:59:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

CTAGAGACTT CGACTTGGAC ATGCT                                   25

(2) INFORMATION FOR SEQ ID NO:60:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

AGTCCCCCAG CATGTCCAAG TCGAAGTCT                               29

(2) INFORMATION FOR SEQ ID NO:61:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:61:

GGGGGACTTC GACTTGGACA TGCTGACTAG TTGAG                                          35

(2) INFORMATION FOR SEQ ID NO:62:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

GATCCTCAAC TAGTCAGCAT GTCCAAGTCG A                                              31

(2) INFORMATION FOR SEQ ID NO:63:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

ATGCTCTAGA GACGGGGATT CCCCGGGGCC G                                              31

(2) INFORMATION FOR SEQ ID NO:64:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:64:

GCATGGATCC TCATTAACTA GTCCCACCGT ACTCGTCAAT TCC                                 43

(2) INFORMATION FOR SEQ ID NO:65:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:65:

CTAGAGACAC CAGTGCCCTG CTGGACCTGT TCAGCCCCTC G                                   41

(2) INFORMATION FOR SEQ ID NO:66:

(i) SEQUENCE CHARACTERISTICS:
        (A) LENGTH: 43 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:66:

GGTCACCGAG GGGCTGAACA GGTCCAGCAG GGCACTGGTG TCT                43

(2) INFORMATION FOR SEQ ID NO:67:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:67:

GTGACCGTGC CCGACATGAG CCTGCCTGAC CTTGACAGCA G                  41

(2) INFORMATION FOR SEQ ID NO:68:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:68:

GTGACCGTGC CCGACATGAG CCTGCCTGAC CTTGACAGCA G                  41

(2) INFORMATION FOR SEQ ID NO:69:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:69:

Ser Arg Asp Phe Ala Asp Met Asp Phe Asp Ala Leu Leu
1               5                   10

(2) INFORMATION FOR SEQ ID NO:70:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:70:

Asp Leu Asp Ser Ser Leu Ala Ser Ile Gln Glu Leu Leu Ser
1               5                   10

(2) INFORMATION FOR SEQ ID NO:71:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:71:

```
Ser Arg Ser Tyr Gly Gln Gln Gly Ser Gly Ser
1               5                   10
```

(2) INFORMATION FOR SEQ ID NO:72:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:72:

```
Asp Phe Asp Leu Asp Met Leu Gly Asp Phe Asp Leu Asp Met Leu Gly
1               5                   10                  15
Ser Arg
```

HETEROLOGOUS TRANSCRIPTION FACTORS

This application claims benefit of Provisional Applications 60/000,553 filed Jun. 27, 1995 and 60/019,614 filed Dec. 29, 1995.

INTRODUCTION

A large number of biological and clinical protocols, among others, gene therapy, production of biological materials, and biological research, depend on the ability to elicit specific and high-level expression of genes encoding RNAs or proteins of therapeutic, commercial, or experimental value. Achieving a sufficiently high level of expression for clinical or other utility in genetically engineered cells within whole organisms has often been a limiting problem. Various approaches for addressing this problem, including the search for stronger transcriptional promoters or higher transfection efficiencies, have in many cases not met with success. Meanwhile, in various lines of research with transcription factors, promising results in transient transfection models have not been borne out with chromosomally integrated reporter gene constructs. Furthermore, overexpression of transcription factors is commonly associated with toxicity to the host cell. Despite those precedents, this invention takes a novel approach to the challenge of optimizing heterologous gene expression through new uses of, and new designs for, transcription factor proteins which are expressed within the engineered cells containing the target gene. The invention provides improved methods and materials for achieving high-level expression of a target gene in genetically engineered cells, including genetically engineered cells within whole organisms.

SUMMARY OF THE INVENTION

This invention involves protein transcription factors, DNA sequences encoding such proteins, transcription control sequences responsive to the transcription factors, target gene constructs containing a target gene operably linked to such a transcription control sequence, cells engineered to contain a target gene construct and to express such the transcription factor, organisms containing such cells and the use of these materials in gene therapy, production of biological materials, and biological research. In order to achieve constitutive expression of a target gene in a cell, preferably a cell within a host organism, one introduces into the organism cells which contain (a) a transcription factor construct containing a first heterologous DNA sequence encoding and capable of expressing a transcription factor capable of activating transcription of a gene linked to a trancription control sequence responsive to the transcription factor, and (b) a target gene construct containing a second heterologous DNA sequence comprising a target gene operably linked to a transcription control sequence comprising a DNA promoter sequence and one or more copies of a DNA recognition sequence permitting gene transcription responsive to the presence of the transcription factor.

Generally the cells are animal cells, preferably syngeneic to the host organism into which the cells are introduced. Host organisms of particular interest are mammals, i.e., post-implantation embryos and especially post-natal mammals. The invention is considered to be of particular significance to the practice of gene therapy with human subjects. In human gene therapy applications the engineered cells will typically be of mammalian origin, preferably human and in some cases autologous to the host.

The transcription factor may be a naturally occurring protein, especially if it is heterologous to the cell type to be engineered. Currently preferred embodiments, however, involve the use of a chimeric transcription factor containing at least two mutually heterologous peptide sequences. The transcription factor will contain one or more DNA-binding domains and one or more transcription activation domains, each of which containing peptide sequence often derived from naturally occurring transcription factors. For example, a fusion protein containing the well-known Herpes simplex virus transcription activation domain, VP16, linked to the bacterial DNA binding domain, GAL4, constitutes such a chimeric transcription factor. Preferably, however, the peptide sequence of each of the domains will be derived from a naturally occurring human peptide sequence. In some embodiments the DNA-binding domain and/or the transcription activation domain comprises a composite domain containing mutually-heterologous and/or reiterated subdomains.

The peptide sequence spanning positions 450 through 550 of human NF-kB p65, for instance, constitutes a transcription activation domain of human origin which may be used in transcription factors of this invention. In some embodiments, a novel, extended p65 sequence, spanning residues 361 through 550, is used. That peptide sequence is referred to herein as "p65(361–550)". In various embodiments the transcription factor contains multiple copies of the transcription activation domain and/or a plurality of different transcription activation domains, subdomains or potentiating motifs. Transcription activation domains comprising a plurality of different and/or reiterated peptide sequences constitute composite transcription activation domains. One illustrative class of composite transcription activation domains comprise one or more copies of (a) the full sequence of p65(361–550), (b) one or more portions of that sequence, or (c) a combination of (a) and (c), together with one or more copies of one or more transcription activation potentiating motifs. Such motifs may be selected or derived from the so-called "proline-rich", "glutamine-rich" and "acidic" activation motifs such as the VP16 V8 motif (DFDLDMLG)[SEQ ID NO:1], the related "V9" motif (DFDLDMLGG) [SEQ ID NO:2] or a human activation motif such as the 14 amino acid acidic motif of human heat shock factor.

Various DNA binding domains may be incorporated into the design of the transcription factor so long as a corresponding DNA "recognition" sequence is known or can be identified to which the domain is capable of binding. One or more copies of the recognition sequence are incorporated into the transcription control sequence of the target gene construct. Again, peptide sequence of human origin is preferred for the DNA binding domain(s). Composite DNA binding domains provide a means for achieving novel sequence specificity for the protein-DNA binding interaction. An illustrative composite DNA binding domain containing component peptide sequences of human origin is ZFHD-1 which is described in detail below. Individual DNA-binding domains may be further modified by mutagenesis to decrease, increase, or change the recognition specificity of DNA binding. These modifications could be achieved by rational design of substitutions in positions known to contribute to DNA recognition (often based on homology to related proteins for which explicit structural data are available). For example, in the case of a homeodomain, substitutions can be made in amino acids in the N-terminal arm, first loop, second helix, and third helix known to contact DNA. In zinc fingers, substitutions can be made at selected positions in the DNA recognition helix.

Alternatively, random methods, such as selection from a phage display library could be used to identify altered domains with increased affinity or altered specificity. Individual DNA-binding domains may be further modified by mutagenesis to decrease, increase, or change the recognition specificity of DNA binding. These modifications could be achieved by rational design of substitutions in positions known to contribute to DNA recognition (often based on homology to related proteins for which explicit structural data are available). For example, in the case of a homeodomain, substitutions can be made in amino acids in the N-terminal arm, first loop, second helix, and third helix known to contact DNA. In zinc fingers, substitutions can be made at selected positions in the DNA recognition helix. Alternatively, random methods, such as selection from a phage display library could be used to identify altered domains with increased affinity or altered specificity.

In one embodiment, the DNA sequence encoding the transcription factor and the DNA sequence encoding the target gene are both operably linked to transcription control sequences containing one or more copies of a common DNA recognition sequence permitting gene expression responsive to the presence of the transcription factor. The two transcription control sequences may contain the same or different promoter sequences.

The cells containing the components mentioned above are prepared by introduction of the desired DNA constructs, linked or unlinked to each other, using any methods and materials permitting introduction of heterologous DNA into cells. For instance, the constructs may be introduced into the cell by calcium phosphate precipitation, DEAE dextran-DNA complexation, fusion, electroporation, biolistics, transfection, lipofection.etc. Various types of DNA vectors are known which may be used, including retroviral, adenoviral, adenoassociated viral, BPV, etc. The engineered cells may be cultured and the introduced DNA may be permitted to integrate into the host cell's chromosomal material. The engineered cells may be characterized as desired and may be encapsulated within a variety of semi-permeable materials prior to introduction into the host organism using known methods.

As an alternative to the introduction of genetically engineered cells into the whole organism, the various DNA constructs may be introduced directly into the host organism using materials, methods and conditions permitting DNA uptake by one or more cells within the organsim, e.g. using direct injection, liposomes, or DNA vectors including viral vectors such as retroviral vectors, adenoviral vectors, or AAV vectors.

Some of the materials invented for use in this invention have significant utility even beyond the scope of constitutive gene therapy and may be used in regulated gene therapy and in other methods and materials relevant to heterologous transcription of a desired gene. Such materials include recombinant DNA molecules encoding chimeric transcription factors containing one or more copies of peptide sequence from within p65(361–450) or containing one or more copies of p65-derived sequence together with one or more copies of one or more heterologous activation motifs. Other broadly useful materials include recombinant DNA molecules containing a target gene operably linked to a minimal IL-2 promoter.

DETAILED DESCRIPTION OF THE INVENTION

Definitions

Figure 1:
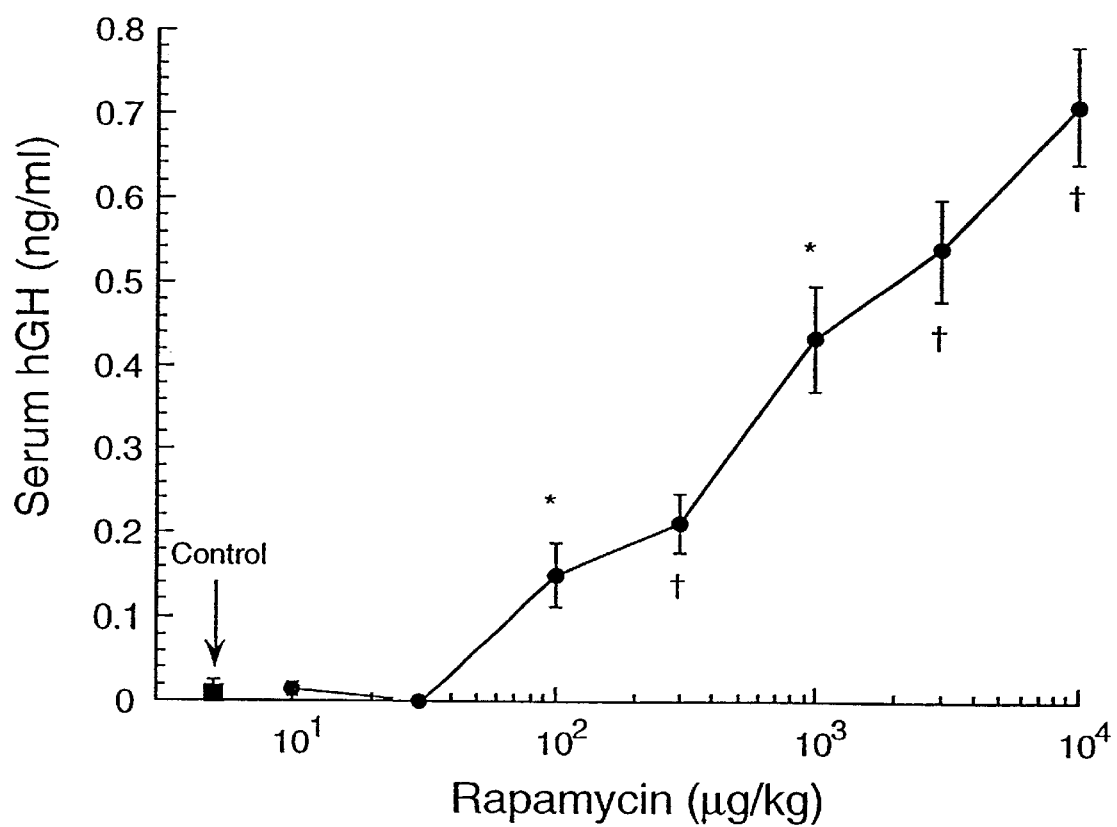
FIG. 1 demonstrates that in vivo administration of a dimerizing agent to animals into which engineered cells had been transplanted led to regulated gene expression and the production and secretion of the gene product. HT1080 cells were transfected with DNA constructs encoding regulatable transcription factor components as described in the examples below. Transfected HT1080 cells ($2 \times 10^6$ total per animal, in four different sites) were injected intramuscularly into male nu/nu mice. Approximately one hour later, animals received the indicated concentration of intravenous rapamycin. Blood samples were collected 17 hours after rapamycin adminsitration and assayed for hGH concentration. Rapamycin treatment produced a dose-dependent increase in serum hGH ($X \pm SEM$; n=at least 5 at each dose).*represent statistical significance from each lower rapamycin dose and † represents statistical significance from rapamycin doses which are 10-fold and more lower ($p < 0.05$, one-way analysis of variance and Tukey-Kramer multiple comparison testing).

The definitions and orienting information below will be helpful for a full understanding of the present disclosure.

"Minimal promoter" as that phrase is used herein means a DNA sequence which is derived from a regulatory region upstream of a gene, contains a TATA box flanked upstream by about 20–30 base pairs and on its 3' end by ~100–300 bp, and which has little or no basal promoter activity, i.e., less than about 1% of the promoter activity observed with the full length regulatory region as determined by any measure of transcriptional activity.

"Derived from" as that phrase is used herein indicates a peptide or nucleotide sequence selected from within a given sequence. A peptide or nucleotide sequence derived from a named sequence may contain a small number of modifications relative to the parent sequence, in most cases representing deletion, replacement or insertion of less than about 15%, preferably less than about 10%, and in many cases less than about 5%, of amino acid residues or base pairs present in the parent sequence. In the case of DNAs, one DNA molecule is also considered to be derived from another if the two are capable of selectively hybridizing to one another.

The terms "chimeric", "fusion", "recombinant", and "composite" are used to denote a protein, peptide domain or nucleotide sequence or molecule containing at least two component portions which are mutually heterologous in the sense that they do not occur together in the same arrangement in nature. More specifically, the component portions are not found in the same continuous polypeptide or gene in nature, at least not in the same order or orientation or with the same spacing present in the chimeric protein or composite domain. Such materials contain components derived from at least two different proteins or genes or from at least two non-adjacent portions of the same protein or gene. Composite proteins, and DNA sequences which encode them, are recombinant in the sense that they contain at least two consituent portions which are not otherwise found directly linked (covalently) together in nature.

"DNA recognition sequence" as that phrase is used herein means a DNA sequence which is capable of binding to one or more DNA-binding domains of a transcription factor.

"Transcription activation motifs" as that phrase is used herein means a peptide motif of at least about 6 amino acid residues associated with a transcription activation domain, including the well-known "acidic", "glutamine-rich" and "proline-rich" motifs such as the K13 motif from p65, the OCT2 Q domain and the OCT2 P domain, respectively.

Components of the System

The system, as employed in cells, comprises: (1) a DNA construct encoding and directing the expression of a transcription factor protein, typically containing at least one DNA-binding domain and one or more transcriptional activation domains; and, (2) a DNA construct containing a target gene and a transcription control sequence permitting transcription of the target gene under the direction of the transcription factor. The transcription control sequence comprises a DNA promoter sequence and one or more copies of a DNA recognition sequence to which the transcription factor is capable of binding.

The transcription factor may be a naturally occurring transcription factor, preferably heterologous with respect to the cells to be engineered. In embodiments of particular interest, the transcription factor is a chimeric protein designed such that it contains at least one DNA binding domain and at least one transcription activation domain which is heterologous with respect to the DNA binding domain. One such hybrid transcription factor contains a GAL4 binding domain fused to a VP16 transcriptional activation domain. It will often be generally preferred that component domains of the transcription factor be derived from proteins endogenous to the cells to be engineered, as described below. This is especially true in the case of gene therapy in human subjects. Well known human transcription factors include p65, p53 and SP1. In the case of the DNA binding domains, however, it is preferable to use a domain which is heterologous with respect to the cells to be engineered. Heterologous DNA binding domains include those which occur naturally in cell types other than the cells to be engineered as well as composite DNA binding domains containing component portions which are riot found in the same continuous polypeptide or gene in nature, at least not in the same order or orientation or with the same spacing present in the composite domain. In the case of composite DNA binding domains, component peptide portions which are endogenous to the cells or organism to be engineered are generally preferred.

1. DNA-binding Domains

Transcription factors of this invention contain one or more DNA binding domains which may be selected from peptide sequences of naturally occurring DNA-binding proteins such as the yeast GAL4 DNA-binding domain, may be derived from such sequences or may comprise a composite DNA-binding region. A composite DNA-binding region consists of a continuous polypeptide region containing two or more component heterologous polypeptide portions which are individually capable of recognizing (i.e., binding to) specific nucleotide sequences. The component polypeptide domains comprise peptide sequence derived from different proteins, peptide sequences from at least two non-adjacent portions of the same protein, polypeptide sequences which are not found so linked in nature (including reiterated copies of a polypeptide sequence) or non-naturally occurring peptide sequence. Preferably the DNA-binding domain or component peptide sequences thereof are selected or derived from peptide sequences endogenous to the cells or organism to be engineered. The individual component portions may be separated by a linker comprising one or more amino acid residues intended to permit the simultaneous contact of each component polypeptide portion with the DNA target. The combined action of the composite DNA-binding region formed by the component DNA-binding modules is thought to result in the addition of the free energy decrement of each set of interactions. The effect is to achieve a DNA-protein interaction of very high affinity, preferably with dissociation constant below $10^{-9}$ M, more preferably below $10^{-10}$ M, even more preferably below $10^{-11}$ M. This goal is often best achieved by combining component polypeptide regions that bind DNA poorly on their own, that is with low affinity, insufficient for functional recognition of DNA under typical conditions in a mammalian cell. Because the hybrid protein exhibits affinity for the composite site several orders of magnitude higher than the affinities of the individual subdomains for their subsites, the protein preferentially (preferably exclusively) occupies the "composite" site which typically comprises a nucleotide sequence spanning the individual DNA sequence recognized by the individual component polypepticle portions of the composite DNA-binding region.

Suitable component DNA-binding polypeptides for incorporation into a composite region have one or more, preferably more, of the following properties. They bind DNA as monomers, although dimers can be accommodated. They should have modest affinities for DNA, with dissociation constants preferably in the range of $10^{-6}$ to $10^{-9}$ M. They should optimally belong to a class of DNA-binding domains whose structure and interaction with DNA are well understood and therefore amenable to manipulation. For gene therapy applications, they are preferably derived from human proteins.

A structure-based strategy of fusing known DNA-binding modules has been used to design transcription factors with novel DNA-binding specificities. In order to visualize how certain DNA-binding domains might be fused to other DNA-binding domains, computer modeling studies have been used to superimpose and align various protein-DNA complexes.

Two criteria suggest which alignments of DNA-binding domains have potential for combination into a composite DNA-binding region (1) lack of collision between domains, and (2) consistent positioning of the carboxyl- and amino-terminal regions of the domains, i.e., the domains must be oriented such that the carboxyl-terminal region of one polypeptide can be joined to the amino-terminal region of the next polypeptide, either directly or by a linker (indirectly). Domains positioned such that only the two amino-terminal regions are adjacent to each other or only the two carboxyl-terminal regions are adjacent to each other are not suitable for inclusion in the chimeric proteins of the present invention. When detailed structural information about the protein-DNA complexes is not available, it may be necessary to experiment with various endpoints, and more biochemical work may be necessary to characterize the DNA-binding properties of the chimeric proteins. This optimization can be performed using known techniques. Virtually any domains satisfying the above-described criteria are candidates for inclusion in the chimeric protein. Alternatively, non-computer modeling may also be used.

2. Examples of Suitable Component DNA-binding Domains

DNA-binding domains with appropriate DNA binding properties may be selected from several different types of natural DNA-binding proteins. One class comprises proteins that normally bind DNA only in conjunction with auxiliary DNA-binding proteins, usually in a cooperative fashion, where both proteins contact DNA and each protein contacts the other. Examples of this class include the homeodomain proteins, many of which bind DNA with low affinity and poor specificity, but act with high levels of specificity in vivo due to interactions with partner DNA-binding proteins. One well-characterized example is the yeast alpha2 protein, which binds DNA only in cooperation with another yeast protein Mcm1. Another example is the human homeodomain protein Phox1, which interacts cooperatively with the human transcription factor, serum response factor (SRF).

The homeodomain is a highly conserved DNA-binding domain which has been found in hundreds of transcription factors (Scott et al., *Biochim. Biophys.* Acta 989:25–48 (1989) and Rosenfeld, *Genes Dev.* 5:897–907 (1991)). The regulatory function of a homeodomain protein derives from the specificity of its interactions with DNA and presumably with components of the basic transcriptional machinery, such as RNA polymerase or accessory transcription factors (Laughon, *Biochemistry* 30(48):11357 (1991)). A typical homeodomain comprises an approximately 61-amino acid residue polypeptide chain, folded into three alhpha helices which binds to DNA.

A second class comprises proteins in which the DNA-binding domain is comprised of multiple reiterated modules that cooperate to achieve high-affinity binding of DNA. An example is the C2H2 class of zinc-finger proteins, which typically contain a tandem array of from two or three to dozens of zinc-finger modules. Each module contains an alpha-helix capable of contacting a three base-pair stretch of DNA. Typically, at least three zinc-fingers are required for high-affinity DNA binding. Therefore, one or two zinc-fingers constitute a low-affinity DNA-binding domain with suitable properties for use as a component in this invention. Examples of proteins of the C2H2 class include TFIIIA, Zif238, Gli, and SRE-ZBP. (These and other proteins and DNA sequences referred to herein are well known in the art. Their sources and sequences are known.)

The zinc finger motif, of the type first discovered in transcription factor IIIA (Miller et al., *EMBO J.* 4:1609 (1985)), offers an attractive framework for studies of transcription factors with novel DNA-binding specificities. The zinc finger is one of the most common eukaryotic DNA-binding motifs (Jacobs, *EMBO J.* 11:4507 (1992)), and this family of proteins can recognize a diverse set of DNA sequences (Pavletich and Pabo, *Science* 261:1701 (1993)). Crystallographic studies of the Zif268-DNA complex and other zinc finger-DNA complexes show that residues at four positions within each finger make most of the base contacts, and there has been some discussion about rules that may explain zinc finger-DNA recognition (Desjarlais and Berg, *PNAS* 89:7345 (1992) and Klevit, *Science* 253:1367 (1991)). However, studies have also shown that zinc fingers can dock against DNA in a variety of ways (Pavletich and Pabo (1993) and Fairall et al., *Nature* 366:483 (1993)).

A third general class comprises proteins that themselves contain multiple independent DNA-binding domains. Often, any one of these domains is insufficient to mediate high-affinity DNA recognition, and cooperation with a covalently linked partner domain is required. Examples include the POU class, such as Oct-1, Oct-2 and Pit-1, which contain both a homeodomain and a POU-specific domain; HNF1, which is organized similarly to the POU proteins; certain Pax proteins (examples: Pax-3, Pax-6), which contain both a homeodomain and a paired box/domain; and XXX, which contains a homeodomain and multiple zinc-fingers of the C2H2 class.

From a structural perspective, DNA-binding proteins containing domains suitable for use as polypeptide components of a composite DNA-binding region may be classified as DNA-binding proteins with a helix-turn-helix structural design, including, but not limited to, MAT a1, MAT a2, MAT a1, Antennapedia, Ultrabithorax, Engrailed, Paired, Fushi tarazu, HOX, Unc86, and the previously noted Oct1, Oct2 and Pit; zinc finger proteins, such as Zif268, SWI5, Krüppel and Hunchback; steroid receptors; DNA-binding proteins with the helix-loop-helix structural design, such as Daughterless, Achaete-scute (T3), MyoD, E12 and E47; and other helical motifs like the leucine-zipper, which includes GCN4, C/EBP, c-Fos/c-Jun and JunB. The amino acid sequences of the component DNA-binding domains may be naturally-occurring or non-naturally-occurring (or modified).

The choice of component DNA-binding domains may be influenced by a number of considerations, including the species, system and cell type which is targeted; the feasibility of incorporation into a chimeric protein, as may be shown by modeling; and the desired application or utility. The choice of DNA-binding domains may also be influenced by the individual DNA sequence specificity of the domain and the ability of the domain to interact with other proteins or to be influenced by a particular cellular regulatory pathway. Preferably, the distance between domain termini is relatively short to facilitate use of the shortest possible linker or no linker. The DNA-binding domains can be isolated from a naturally-occurring protein, or may be a synthetic molecule based in whole or in part on a naturally-occurring domain.

An additional strategy for obtaining component DNA-binding domains with properties suitable for this invention is to modify an existing DNA-binding domain to reduce its affinity for DNA into the appropriate range. For example, a homeodomain such as that derived from the human transcription factor Phox1, may be modified by substitution of the glutamine residue at position 50 of the homeodomain. Substitutions at this position remove or change an important point of contact between the protein and one or two base pairs of the 6-bp DNA sequence recognized by the protein. Thus, such substitutions reduce the free energy of binding and the affinity of the interaction with this sequence and may or may not simultaneously increase the affinity for other sequences. Such a reduction in affinity is sufficient to effectively eliminate occupancy of the natural target site by this protein when produced at typical levels in mammalian cells. But it would allow this domain to contribute binding energy to and therefore cooperate with a second linked DNA-binding domain. Other domains that amenable to this type of manipulation include the paired box, the zinc-finger class represented by steroid hormone receptors, the myb domain, and the ets domain.

Illustrating the class of chimeric proteins of this invention which contain a composite DNA-binding domain comprising at least one homeodomain and at least one zinc finger domain are a set of chimeric proteins in which the composite DNA-binding region comprises an Oct-1 homeodomain and zinc fingers 1 and 2 of Zif268, referrred to herein as "ZFHD1". Proteins comprising the ZFHD1 composite DNA-binding region have been produced and shown to bind a composite DNA sequence,

```
5' TAATTANGGGNG 3'     [SEQ ID NO:3]

3' ATTAATNCCCNC 5'
``` which includes the nucleic acid sequences bound by the relevant portion of the two component DNA-binding proteins.

3. Design of Linker Sequence for Covalently Linked Composite DNA-binding Domains The continuous polypeptide span of a composite DNA-binding domain may contain the component polypeptide modules linked directly end-to-end or linked indirectly via an intervening amino acid or peptide linker. A linker moiety may be designed or selected empirically to permit the independent interaction of each component DNA-binding domain with DNA without steric interference. A linker may also be selected or designed so as to impose specific spacing and orientation on the DNA-binding domains. The linker amino acids may be derived from endogenous flanking peptide sequence of the component domains or may comprise one or more heterologous amino acids. Linkers may be designed by modeling or identified by experimental trial.

The linker may be any amino acid sequence that results in linkage of the component domains such that they retain the ability to bind their respective nucleotide sequences. In some embodiments it is preferable that the design involve an arrangement of domains which requires the linker to span a relatively short distance, preferably less than about 10 Å. However, in certain embodiments, depending upon the selected DNA-binding domains and the configuration, the linker may span a distance of up to about 50 Å. For instance, the ZFHD1 protein contains a glycine-glycine-arginine-arginine linker which joins the carboxyl-terminal region of zinc finger 2 to the amino-terminal region of the Oct-1 homeodomain.

Within the linker, the amino acid sequence may be varied based on the preferred characteristics of the linker as determined empirically or as revealed by modeling. For instance, in addition to a desired length, modeling studies may show that side groups of certain nucleotides or amino acids may interfere with binding of the protein. The primary criterion is that the linker join the DNA-binding domains in such a manner that they retain their ability to bind their respective DNA sequences, and thus a linker which interferes with this ability is undesirable. A desirable linker should also be able to constrain the relative three-dimensional positioning of the domains so that only certain composite sites are recognized by the chimeric protein. Other considerations in choosing the linker include flexibility of the linker, charge of the linker and selected binding domains, and presence of some amino acids of the linker in the naturally-occurring domains. The linker can also be designed such that residues in the linker contact DNA, thereby influencing binding affinity or specificity, or to interact with other proteins. For example, a linker may contain an amino acid sequence which can be recognized by a protease so that the activity of the chimeric protein could be regulated by cleavage. In some cases, particularly when it is necessary to span a longer distance between the two DNA-binding domains or when the domains must be held in a particular configuration, the linker may optionally contain an additional folded domain.

4. Optimization and Engineering of Composite DNA-binding Regions

The useful range of composite DNA binding regions is not limited to the specifities that can be obtained by linking two naturally occurring DNA binding subdomains. A variety of mutagenesis methods can be used to alter the binding specificity. These include use of the crystal or NMR structures (3D) of complexes of a DNA-binding domain with DNA to rationally predict (an) amino acid substitution(s) that will alter the nucleotide sequence specificity of DNA binding, in combination with computational modelling approaches. Candidate mutants can then be engineered and expressed and their DNA binding specificity identified using oligonucleotide site selection and DNA sequencing, as described earlier.

An alternative approach to generating novel sequence specificities is to use databases of known homologs of the DNA-binding domain to predict amino acid substitutions that will alter binding. For example, analysis of databases of zinc finger sequences has been used to alter the binding specificity of a zinc finger (Desjarlais and Berg (1993) *Proc. Natl. Acad. Sci. USA* 90, 2256–2260).

A further and powerful approach is random mutaganesis of amino acid residues which may contact the DNA, followed by screening or selection for the desired novel specificity. Preferably, the libraries are surveyed using phage display so that mutants can be directly selected. For example, phage display of the three fingers of Zif268 (including the two incorporated into ZFHD1) has been described, and random mutagenesis and selection has been used to alter the specificity and affinity of the fingers (Rebar and Pabo (1994) *Science* 263, 671–673; Jamieson et al, (1994) Biochemistry 33, 5689–5695; Choo and Klug (1994) *Proc. Natl. Acad. Sci. USA* 91, 11163–11167; Choo and Klug (1994) *Proc. Natl. Acad. Sci. USA* 91, 11168–11172; Choo et al (1994) Nature 372, 642–645; Wu et al (1995) Proc. Natl. Acad. Sci USA 92, 344–348). These mutants can be incorporated into ZFHD1 to provide new composite DNA binding regions with novel nucleotide sequence specificities. Other DNA-binding domains may be similarly altered. If structural information is not available, general mutagenesis strategies can be used to scan the entire domain for desirable mutations: for example alanine-scanning mutagenesis (Cunningham and Wells (1989) Science 244, 1081–1085), PCR misincorporation mutagenesis (see eg. Cadwell and Joyce (1992) PCR Meth. Applic. 2, 28–33), and 'DNA shuffling' (Stemmer (1994) *Nature* 370, 389–391). These techniques produce libraries of random mutants, or sets of single mutants, that can then be readily searched by screening or selection approaches such as phage display.

In all these approaches, mutagenesis can be carried out directly on the composite DNA binding region, or on the individual subdomain of interest in its natural or other protein context. In the latter case, the engineered component domain with new nucleotide sequence specificity may be subsequently incorporated into the composite DNA binding region in place of the starting component. The new DNA binding specificity may be wholly or partially different from that of the initial protein: for example, if the desired binding specificity contains (a) subsite(s) for known DNA binding subdomains, other subdomains can be mutated to recognize adjacent sequences and then combined with the natural domain to yield a composite DNA binding region with the desired specificity.

Randomization and selection strategies may be used to incorporate other desirable properties into the composite DNA binding regions in addition to altered nucleotide recognition specificity, by imposing an appropriate in vitro selective pressure (for review see Clackson and Wells (1994) Trends Biotech. 12, 173–184). These include improved affinity, improved stability and improved resistance to proteolytic degradation.

Overall, in designing or optimizing chimeric proteins of this invention it should be appreciated that immunogenicity of a polypeptide sequence is thought to require the binding of peptides by MHC proteins and the recognition of the presented peptides as foreign by endogenous T-cell receptors. It may be preferable, at least in gene therapy applications, to alter a given foreign peptide sequence to minimize the probability of its being presented in humans.

For example, peptide binding to human MHC class I molecules has strict requirements for certain residues at key 'anchor' positions in the bound peptide: eg. HLA-A2 requires leucine, methionine or isoleucine at position 2 and leucine or valine at the C-terminus (for review see Stern and Wiley (1994) Structure 2, 145–251). Thus in engineered proteins, this periodicity of those residues could be avoided.

5. Transcriptional Activation Domains

Transcription factors of this invention also contain one or more transcription activation domains which may be selected from peptide sequences of naturally occurring transcription factors such as the widely used transcription activation domain of Herpes Simplex Virus VP16, may be derived from such sequences or may comprise a composite transcription activation region. A composite transcription activation region consists of a continuous polypeptide region containing two or more reiterated or mutually heterologous component polypeptide portions. The component polypeptide portions comprise polypeptide sequences derived from at least two different proteins, polypeptide sequences from at least two non-adjacent portions of the same protein, polypeptide sequences which are not found so linked in nature (including reiterated copies of a polypeptide sequence) or non-naturally occurring peptide sequence. Preferably the activation domain or component peptide sequences thereof are selected or derived from peptide sequences endogenous to the cells or organism to be engineered.

One particularly important source of transcription activation domains which are featured in a number of embodiments of the invention is human NF-kB p65. In one embodiment the transcription factor contains one or more copies of a poptide sequence comprising all or part of the p65 sequence spanning residues 450–550, or a peptide sequence derived therefrom, together with peptide sequence heterologous thereto. That heterologous sequence includes one or more DNA binding domains as discussed elsewhere and may further include, inter alia, additional activation domains. p65(450–550) is a known transcription activation domain although methods and materials for using it as described herein have not been previously reported. We have found that extending the p65 peptide sequence to include sequence spanning p65 residues 361–450 leads to an unexpected increase in transcription activation. Moreover, a peptide sequence comprising all or a portion of p65 (361–550), or peptide sequence derived therefrom, in combination with heterologous activation motifs, can yield surprising additional increases in the level of transcription activation. p65-based activation domains function across a broad range of promoters and have yielded increases in transcription levels six-fold, eight-fold and even 14–15-fold higher than obtained with tandem copies of VP16 which itself is widely recognized as a very potent activation domain.

While the resultant increases in activation potency are dramatic, p65-based transcription factors possess additional and unexpected characteristics. For instance, unlike VP16, our p65-based activators do not appear to be toxic to the engineered cells. This is clearly of profound practical significance in many applications. It is expected that recombinant DNA molecules encoding chimeric proteins which contain a peptide sequence comprising all or a portion of p65(361–550), especially containing one or more portions of the sequence spanning residues 361 and 450, or peptide sequence derived therefrom, will provide significant advantages for heterologous gene expression in its various contexts, including constitutive systems such as described herein, as well as in regulated systems such as described in International patent applications PCT/US94/01617, PCT/US95/10591, PCT/US96/- - -(Atty docket ARIAD 345-B-PCT, entitled "Rapamycin-based Regulation of Biological Events", filed Jun. 7, 1996) and the like, as well as in other heterologous transcription systems such as those involving tetracylin-based regulation reported by Bujard et al. and those involving steroid or other hormone-based regulation.

One class of p65-based transcription factors contain more than one copy of a p65-derived domain. Such proteins will typically contain two to about six copies of a peptide sequence comprising all or a portion of p65(361–550), or peptide sequence derived therefrom. Such transcription factors may contain one or more DNA-binding domains, a ligand-binding domain to provide for regulation e.g. by any of the previously mentioned systems.

Transcription factors of this invention may contain, in addition to one or more copies of a primary activation domain such as described above, one or more copies of one or more heterologous peptide sequences which potentiate the transcription activation potency of the transcription factor, as measured by any means. Inclusion of such motifs, including the socalled "glutamine-rich", "proline-rich" and "acidic" trarscription activation motifs, in combination with a primary activation domain can result in extremely high levels of transcription.

Illustrative activation domains and motifs of human origin-include the activation domain of human CTF, the 18 amino acid (NFLQLPQQTQGALLTSCQP)[SEQ ID NO:4] glutamine rich region of Oct-2, the N-terminal 72 aminoacids of p53, the SYGQQS[SEQ ID NO:5] repeat in Ewing sarcoma gene and an 11 amino acid (535–545) acidic rich region of Rel A protein.

Illustrating the class of chimeric proteins of this invention which contain a composite DNA-binding domain and at least one transcription activation domain are chimeric proteins containing the ZFHD1 composite DNA-binding region and the Herpes Simplex Virus VP16 activation domain, which has been produced and shown to activate transcription selectively in vivo of a gene (the luciferase gene) linked to an iterated ZFHD1 binding site. Another chimeric protein containing ZFHD1 and an NF-kB p65(450–550) activation domain has also been produced and shown to activate transcription in vivo of a gene (secreted alkaline phosphatase) linked to iterated ZFHD1 binding sites. Various additional activation domains, motifs and chimeric transcription factors are provided in the examples which follow.

6. Additional Domains

Additional domains may be included in chimeric proteins of this invention. For example, the chimeric proteins may contain a nuclear localization sequence which provides for the protein to be translocated to the nucleus. Typically a nuclear localization sequence has a plurality of basic amino acids, referred to as a bipartite basic repeat (reviewed in Garcia-Bustos et al, Biochimica et Biophysica Acta (1991) 1071, 83–101). This sequence can appear in any portion of the molecule internal or proximal to the N- or C-terminus and results in the chimeric protein being localized inside the nucleus.

The chimeric proteins may include domains that facilitate their purification, e.g. "histidine tags" or a glutathione-S-transferase domain. They may include "epitope tags" encoding peptides recognized by known monoclonal antibodies for the detection of proteins within cells or the capture of proteins by antibodies in vitro.

Transcription factors can be tested for activity in vivo using a simple assay (F.M. Ausubel et al., Eds., CURRENT PROTOCOLS IN MOLECULAR BIOLOGY (John Wiley & Sons, New York, 1994); de Wet et al., *Mol. Cell Biol.* 7:725 (1987)). The in vivo assay requires a plasmid containing and capable of directing the expression of a recombinant DNA sequence encoding the transcription factor. The assay also requires a plasmid containing a reporter gene, e.g., the luciferase gene, the chloramphenicol acetyl transferase (CAT) gene, secreted alkaline phosphatase or the human growth hormone (hGH) gene, linked to a binding site for the transcription factor. The two plasmids are introduced into host cells which normally do not produce interfering levels of the reporter gene product. A second group of cells, which also lack both the gene encoding the transcription factor and the reporter gene, serves as the control group and receives a plasmid containing the gene encoding the transcription factor and a plasmid containing the test gene without the binding site for the transcription factor.

The production of mRNA or protein encoded by the reporter gene is measured. An increase in reporter gene expression not seen in the controls indicates that the transcription factor is a positive regulator of transcription. If reporter gene expression is less than that of the control, the transcription factor is a negative regulator of transcription.

Optionally, the assay may include a transfection efficiency control plasmid. This plasmid expresses a gene product independent of the test gene, and the amount of this gene product indicates roughly how many cells are taking up the plasmids and how efficiently the DNA is being introduced into the cells. Additional guidance on evaluating chimeric proteins of this invention is provided below.

7. Transcription Factors, Additional Comments

In engineering cells for or in whole animals in accordance with this invention, it will often be preferred, and in some cases required, that the various domains or subdomains of the chimeric transcription factors be derived from proteins of the same species as the host cell. Thus, for genetic engineering of human cells, it is often preferred that component peptide sequences of human origin be used in some or all cases, rather than of bacterial, yeast or other non-human source. Transcription factor constructs generally contain (1) a promoter region consisting minimally of a TATA box and initiator sequence but optionally including other transcription factor binding sites; (2) DNA sequence encoding the desired transcription factor, including sequences that promote the initiation and termination of translation, if appropriate; (3) an optional sequence consisting of a splice donor, splice acceptor, and intervening intron DNA; and (4) a sequence directing cleavage and polyadenylation of the resulting RNA transcript. The practitioner may select a conventional promoter such as the widely used hCMV promoter region It will be preferred in certain embodiments, especially where DNA is introduced into an animal for uptake by cells in situ, that the transcription factors be expressed in a cell-specific or tissue-specific manner. Such specificity of expression may be achieved by operably linking one or more of the DNA sequences encoding the chimeric protein(s) to a cell-type specific transcriptional regulatory sequence (e.g. promoter/enhancer). Numerous cell-type specific transcriptional regulatory sequences are known. Others may be obtained from genes which are expressed in a cell-specific manner. See e.g. PCT/US95/10591, especially pp. 36–37.

For example, constructs for expressing the chimeric proteins may contain regulatory sequenc derived from known genes for specific expression in selected tissues. Representative examples are tabulated below:

| Tissue | Gene | Reference |
|---|---|---|
| lens | g2-crystallin | Breitman, M. L., Clapoff, S., Rossant, J., Tsui, L. C., Golde, L. M., Maxwell, I. H., Bernstin, A. (1987) Genetic Ablation: targeted expression of a toxin gene causes microphthalmia in transgenic mice Science 238: 1563–1565 |
| | aA-crystallin | Landel, C. P., Zhao, J., Bok, D., Evans, G. A. (1988) Lens-specific expression of a recombinant ricin induces developmental defects in the eyes of transgenic mice. Genes Dev. 2: 1168–1178 Kaur, S., key, B., Stock, J., McNeish, J. D., Akeson, R., Potter, S. S. (1989) Targeted ablation of alpha-crystallin-synthesizing cells produces lens-deficient eyes in transgenic mice. Development 105 613–619 |
| pituitary - somatrophic cells | Growth hormone | Behringer, R. R., Mathews, L. S., Palmiter, R. D., Brinster, R. L. (1988) Dwarf mice produced by genetic ablation of growth hormone-expressing cells. Genes Dev. 2: 453–461 |
| pancreas | Insulin-Elastase - acinar cell specific | Ornitz, D. M., Palmiter, R. D., Hammer, R. E., Brinster, R. L., Swift, G. H., MacDonald, R. J. (1985) Specific expression of an elastase-human growth fusion in pancreatic acinar cells of transgeneic mice Nature 131: 600–603 Palmiter, R. D., Behringer, R. R., Quaife, C. J., Maxwell, F., Maxwell I. H., Brinster, R. L. (1987) Cell lineage ablation in transgeneic mice by cell-specific expression of a toxin gene. Cell 50: 435–443 |
| T cells | lck promoter | Chaffin, K. E., Beals, C. R., Wilkie, T. M., Forbush, K. A., Simon, M. I. Perlmutter, R. M. (1990) EMBO Journal 9: 3821–3829 |
| B cells | Immunoglobulin kappa chain | Borelli, E. Heyman, R., Hsi, M., Evans, R. M. (1988) Targeting of inducible toxic phenotype in animal cells. Proc. Natl. Acad. Sci. USA 85: 7572–7576 Heyman, R. A., Borrelli, E., Lesley, J., Anderson, D., Richmond, D. E., Baird, S. M., Hyman, R., Evans, R. M. (1989) Thymidine kinase obliteration: creation of transgenic mice with controlled immunodeficiencies. Proc. Natl. Acad. Sci. USA 86: 2698–2702 |
| Schwann cells | $P_0$ promoter | Messing, A., Behringer, R. R., Hammang, J. P. Palmiter, R D, Brinster, R L, Lemke, G., $P_0$ promoter directs espression of report and toxin genes to Schwann cells of transgenic mice. Neuron 8: 507–520 1992 |
| | Myelin basic protein | Miskimins, R. Knapp, L., Dewey, M J, Zhang, X. Cell and tissue-specific expression of a heterologous gene under control of the mye basic protein gene promoter in |

-continued

| Tissue | Gene | Reference |
|---|---|---|
| | | trangenic mice. Brain Res Dev Brain Res 1992 Vol 65: 217–21 |
| spermatids | protamine | Breitman, M. L., Rombola, H., Maxwell, I. H., Klintworth, G. K., Bernstein, A. (1990) Genetic ablation in transgenic mice with attenuated diphtheria toxin A gene. Mol. Cell. Biol. 10: 474–479 |
| lung | Lung surfacant gene | Ornitz, D. M., Palmiter, R. D., Hammer, R. E., Brinster, R. L., Swift, G. H., MacDonald, R. J. (1985) Specific expression of an elastase-human growth fusion in pancreatic acinar cells of transgeneic mice Nature 131: 600–603 |
| adipocyte P2 | | Ross, S. R, Braves, R A, Spiegelman, B M Targeted expression of a toxin gene to adipose tissue: transgenic mice resistant to obesity Genes and Dev 7: 1318–24 1993 |
| muscle | myosin light chain | Lee, K J, Ross, R S, Rockman, H A, Harris, A N, O'Brien, T X, van-Bilsen, M., Shubeita, H E, Kandolf, R., Brem, G., Prices et al J. Biol. Chem. 1992 Aug 5, 267: 15875–85 |
| | Alpha actin | Muscat, G E., Perry, S., Prentice, H. Kedes, L. The human skeletal alpha-actin gene is regulated by a muscle-specific enhancer that binds three nuclear factors. Gene Expression 2, 111–26, 1992 |
| neurons | neurofilament protein | Rieben, M. Halmekyto, M. Alhonen, L. Sinervirta, R. Saarma, M. Janne, J. Tissue-specific expression of rat light neurofilament promoter-driven reporter gene in transgenic mice. BBRC 1993: 192: 465–70 |
| liver | tyrosine aminotransferase, albumin, apolipoproteins | |

8. Target Gene Constructs

A DNA construct that enables transcription of a target gene to be regulated by a transcription factor in accordance with this invention comprises a DNA molecule which includes a synthetic transcription unit typically consisting of: (1) one copy or multiple copies of a DNA sequence recognized with high-affinity by the transcription factor or one or more of its component DNA binding domains; (2) a promoter sequence consisting minimally of a TATA box and initiator sequence but optionally including other transcription factor binding sites; (3) sequence encoding the desired product, including sequences that promote the initiation and termination of translation, if appropriate; (4) an optional sequence consisting of a splice donor, splice acceptor, and intervening intron DNA; and (5) a sequence directing cleavage and polyadenylation of the resulting RNA transcript. Typically the gene construct contains a copy of the target gene to be expressed, operably linked to a transcription control sequence comprising a minimal promoter and one or more copies of a DNA recognition sequence responsive to the transcription factor.

(a) Target Genes

A wide variety of genes can be employed as the target gene, including genes that encode a therapeutic protein, antisense sequence or ribozyme of interest. The target gene can be any sequence of interest which provides a desired phenotype. It can encode a surface membrane protein, a secreted protein, a cytoplasmic protein, or there can be a plurality of target genes encoding different products. The target gene may be an antisense sequence which can modulate a particular pathway by inhibiting a transcriptional regulation protein or turn on a particular pathway by inhibiting the translation of an inhibitor of the pathway. The target gene can encode a ribozyme which may modulate a particular pathway by interfering, at the RNA level, with the expression of a relevant transcriptional regulator or with the expression of an inhibitor of a particular pathway. The proteins which are expressed, singly or in combination, can involve homing, cytotoxicity, proliferation, immune response, inflammatory response, clotting or dissolving of clots, hormonal regulation, etc. The proteins expressed may be naturally-occurring proteins, mutants of naturally-occurring proteins, unique sequences, or combinations thereof.

Various secreted products include hormones, such as insulin, human growth hormone, glucagon, pituitary releasing factor, ACTH, melanotropin, relaxin, etc.; growth factors, such as EGF, IGF-1, TGF-a, -b, PDGF, G-CSF, M-CSF, GM-CSF, FGF, erythropoietin, thrombopoietin, megakaryocytic stimulating and growth factors, etc.; interleukins, such as IL-1 to -13; TNF-a and -b, etc.; and enzymes and other factors, such as tissue plasminogen activator, members of the complement cascade, performs, superoxide dismutase, coagulation factors, antithrombin-III, Factor VIIIc, Factor VIIIvW, Factor IX, a -anti-trypsin, protein C, protein S, endorphins, dynorphin, bone morphogenetic protein, CFTR, etc.

The gene can encode a naturally-occurring surface membrane protein or a protein made so by introduction of an appropriate signal peptide and transmembrane sequence. Various such proteins include homing receptors, e.g. L-selectin (Mel-14), blood-related proteins, particularly having a kringle structure, e.g. Factor VIIIc, Factor VIIIvW, hematopoietic cell markers, e.g. CD3, CD4, CD8, B cell receptor, TCR subunits a, b, g, d , CD10, CD19, CD28, CD33, CD38, CD41, etc., receptors, such as the interleukin receptors IL-2R, IL-4R, etc., channel proteins, for influx or efflux of ions, e.g. $H^+$, $Ca^{+2}$, $K^+$, $Na^+$, $Cl^-$, etc., and the like; CFTR, tyrosine activation motif, zap-70, etc.

Proteins may be modified for transport to a vesicle for exocytosis. By adding the sequence from a protein which is directed to vesicles, where the sequence is modified proximal to one or the other terminus, or situated in an analogous position to the protein source, the modified protein will be directed to the Golgi apparatus for packaging in a vesicle. This process in conjunction with the presence of the chimeric proteins for exocytosis allows for rapid transfer of the proteins to the extracellular medium and a relatively high localized concentration.

Also, intracellular proteins can be of interest, such as proteins in metabolic pathways, regulatory proteins, steroid receptors, transcription factors, etc., depending upon the nature of the host cell. Some of the proteins indicated above can also serve as intracellular proteins.

By way of further illustration, in T-cells, one may wish to introduce genes encoding one or both chains of a T-cell receptor. For B-cells, one could provide the heavy and light chains for an immunoglobulin for secretion. For cutaneous cells, e.g. keratinocytes, particularly stem cells keratinocytes, one could provide for protection against infection, by secreting a -, b- or -g interferon, antichemotactic factors, proteases specific for bacterial cell wall proteins, etc.

In addition to providing for expression of a gene having therapeutic value, there will be many situations where one may wish to direct a cell to a particular site. The site can include anatomical sites, such as lymph nodes, mucosal tissue, skin, synovium, lung or other internal organs or functional sites, such as clots, injured sites, sites of surgical manipulation, inflammation, infection, etc. By providing for expression of surface membrane proteins which will direct the host cell to the particular site by providing for binding at the host target site to a naturally-occurring epitope, localized concentrations of a secreted product can be achieved. Proteins of interest include homing receptors, e.g. L-seleclin, GMP140, CLAM-1, etc., or addressing, e.g. ELAM-1, PNAd, LNAd, etc., clot binding proteins, or cell surface proteins that respond to localized gradients of chemotactic factors. There are numerous situations where one would wish to direct cells to a particular site, where release of a therapeutic product could be of great value.

(b) Minimal Promoters

Minimal promoters may be selected from a wide variety of known sequences, including promoter regions from fos, hCMV, SV40 and IL-2, among many others. Illustrative examples are provided which use a minimal CMV promoter or a minimal IL2 gene promoter (−72 to +45 with respect to the start site; Siebenlist et al., MCB 6:3042–3049, 1986)

(c) DNA recognition Sequences

Recognition sequences for a wide variety of DNA-binding domains are known. DNA recognition sequences for other DNA binding domains may be determined experimentally. In the case of a composite DNA binding domain, DNA recognition sequences can be determined experimentally, as described below, or the proteins can be manipulated to direct their specificity toward a desired sequence. A desirable nucleic acid recognition sequence for a composite DNA binding domain consists of a nucleotide sequence spanning at least ten, preferably eleven, and more preferably twelve or more bases. The component binding portions (putative or demonstrated) within the nucleotide sequence need not be fully contiguous; they may be interspersed with "spacer" base pairs that need not be directly contacted by the chimeric protein but rather impose proper spacing between the nucleic acid subsites recognized by each module. These sequences should not impart expression to linked genes when introduced into cells in the absence of the engineered DNA-binding protein.

To identify a nucleotide sequence that is recognized by a chimeric protein containing a DNA-binding region, preferably recognized with high affinity (dissociation constant $10^{-11}$ M or lower are especially preferred), several methods can be used. If high-affinity binding sites for individual subdomains of a composite DNA-binding region are already known, then these sequences can be joined with various spacing and orientation and the optimum configuration determined experimentally (see below for methods for determining affinities). Alternatively, high-affinity binding sites for the protein or protein complex can be selected from a large pool of random DNA sequences by adaptation of published methods (Pollock, R. and Treisman, R., 1990, A sensitive method for the determination of protein-DNA binding specificities. *Nucl. Acids Res.* 18, 6197–6204). Bound sequences are cloned into a plasmid and their precise sequence and affinity for the proteins are determined. From this collection of sequences, individual sequences with desirable characteristics (i.e., maximal affinity for composite protein, minimal affinity for individual subdomains) are selected for use. Alternatively, the collection of sequences is used to derive a consensus sequence that carries the favored base pairs at each position. Such a consensus sequence is synthesized and tested to confirm that it has an appropriate level of affinity and specificity.

The target gene constructs may contain multiple copies of a DNA recognition sequence. For instance, the constructs may contain 5, 8, 10 or 12 recognition sequences for GAL4 or for ZFHD1.

(d) Determination of Binding Affinity

A number of well-characterized assays are available for determining the binding affinity, usually expressed as dissociation constant, for DNA-binding proteins and the cognate DNA sequences to which they bind. These assays usually require the preparation of purified protein and binding site (usually a synthetic oligonucleotide) of known concentration and specific activity. Examples include electrophoretic mobility-shift assays, DNaseI protection or "footprinting", and filter-binding. These assays can also be used to get rough estimates of association and dissociation rate constants. These values may be determined with greater precision using a BIAcore instrument. In this assay, the synthetic oligonucleotide is bound to the assay "chip," and purified DNA-binding protein is passed through the flow-cell. Binding of the protein to the DNA immobilized on the chip is measured as an increase in refractive index. Once protein is bound at equilibrium, buffer without protein is passed over the chip, and the dissociation of the protein results in a return of the refractive index to baseline value. The rates of association and dissociation are calculated from these curves, and the affinity or dissociation constant is calculated from these rates. Binding rates and affinities for the high affinity composite site may be compared with the values obtained for subsites recognized by each subdomain of the protein. As noted above, the difference in these dissociation constants should be at least two orders of magnitude and preferably three or greater.

(e) Testing for Function in vivo

Several tests of increasing stringency may be used to confirm the satisfactory performance of a DNA-binding protein designed according to this invention. All share essentially the same components: (1) (a) an expression plasmid directing the production of a chimeric protein comprising the DNA-binding region and a transcriptional activation domain or (b) one or more expression plasmids directing the production of a pair of chimeric proteins of this invention which are capable of dimerizing in the presence of a corresponding dimerizing agent, and thus forming a protein complex containing a DNA-binding region on one protein and a transcription activation domain on the other; and (2) a reporter plasmid directing the expression of a reporter gene, preferably identical in design to the target gene described above (i.e., multiple binding sites for the DNA-binding domain, a minimal promoter element, and a gene body) but encoding any conveniently measured protein.

In a transient transfection assay, the above-mentiotied plasmids are introduced together into tissue culture cells by any conventional transfection procedure, including for example calcium phosphate coprecipitation, electroporation, and lipofection. After an appropriate time period, usually 24–48 hr, the cells are harvested and assayed for production of the reporter protein. In embodiments requiring dimerization of chimeric proteins for activation of transcription, the assay is conducted in the presence of the dimerizing agent. In an appropriately designed system, the reporter gene should exhibit little activity above background in the absence of any co-transfected plasmid for the composite transcription factor (or in the absence of dimerizing agent in embodiments under dimerizer control). In contrast, reporter gene expression should be elevated in a dose-dependent fashion by the inclusion of the plasmid encoding the composite transcription factor (or plasmids encoding the multimerizable chimeras, following addition of multimerizing agent). This result indicates that there are few natural transcription factors in the recipient cell with the potential to recognize the tested binding site and activate transcription and that the engineered DNA-binding domain is capable of binding to this site inside living cells.

The transient transfection assay is not an extremely stringent test in most cases, because the high concentrations of plasmid DNA in the transfected cells lead to unusually high concentrations of the DNA-binding protein and its recognition site, allowing functional recognition even with relative low affinity interactions. A more stringent test of the system is a transfection that results in the integration of the introduced DNAs at near single-copy. Thus, both the protein concentration and the ratio of specific to non-specific DNA sites would be very low; only very high affinity interactions would be expected to be productive. This scenario is most readily achieved by stable transfection in which the plasmids are transfected together with another DNA encoding an unrelated selectable marker (e.g., G418-resistance). Transfected cell clones selected for drug resistance typically contain copy numbers of the nonselected plasmids ranging from zero to a few dozen. A set of clones covering that range of copy numbers can be used to obtain a reasonably clear estimate of the efficiency of the system.

Perhaps the most stringent test involves the use of a viral vector, typically a retrovirus, that incorporates both the reporter gene and the gene encoding the composite transcription factor or multimerizable components thereof. Virus stocks derived from such a construction will generally lead to single-copy transduction of the genes.

If the ultimate application is gene therapy, it may be preferred to construct transgenic animals carrying similar DNAs to determine whether the protein is functional in an animal.

Design and Assembly of the DNA Constructs

Constructs may be assembled in accordance with the design principles, and using materials and methods, disclosed in the cited patent documents and scientific literature, each of which is incorporated herein by reference, with modifications as described herein. In the case of DNA constructs encoding chimeric transcription factors, DNA sequences encoding individual domains, sub-domains and linkers, if any, are joined such that they constitute a single open reading frame encoding a chimeric protein capable of being translated in cells or cell lysates into a single polypeptide harboring all component domains. The DNA construct encoding the chimeric protein is then placed into a conventional plasmid vector that directs the expression of the protein in the appropriate cell type. For testing of proteins and determination of binding specificity and affinity, it may be desirable to construct plasmids that direct the expression of the protein in bacteria or in reticulocyte-lysate systems. For use in the production of proteins in mammalian cells, the protein-encoding sequence is introduced into an expression vector that directs expression in these cells. Expression vectors suitale for such uses are well known in the art. Various sorts of such vectors are commercially aviailable.

Introduction of Constructs into Cells

This invention is particularly useful for the engineering of animal cells and in applications involving the use of such engineered animal cells. The animal cells may be insect, worm or mammalian cells. While various mammalian cells may be used, including, by way of example, equine, bovine, ovine, canine, feline, murine, and non-human primate cells, human cells are of particular interest. Among the various species, various types of cells may be used, such as hematopoietic, neural, glial, mesenchymal, cutaneous, mucosal, stromal, muscle (including smooth muscle cells), spleen, reticuloendothelial, epithelial, endothelial, hepatic, kidney, gastrointestinal, pulmonary, fibroblast, and other cell types. Of particular interest are hematopoietic cells, which may include any of the nucleated cells which may be involved with the erythroid, lymphoid or myelomonocytic lineages, as well as myoblasts and fibroblasts. Also of interest are stem and progenitor cells, such as hematopoietic, neural, stromal, muscle, hepatic, pulmonary, gastrointestinal and mesenchymal stern cells The cells may be autologous cells, syngeneic cells, allogeneic cells and even in some cases, xenogeneic cells with respect to an intended host organism. The cells may be modified by changing the major histocompatibility complex ("MHC") profile, by inactivating $beta_2$-microglobulin to prevent the formation of functional Class I MHC molecules, inactivation of Class II molecules, providing for expression of one or more MHC molecules, enhancing or inactivating cytotoxic capabilities by enhancing or inhibiting the expression of genes associated with the cytotoxic activity, or the like.

In some instances specific clones or oligoclonal cells may be of interest, where the cells have a particular specificity, such as T cells and B cells hiving a specific antigen specificity or homing target site specificity.

Constructs encoding the transcription factor and target gene construct of this invention can be introduced into the cells as one or more DNA molecules or constructs, in many cases in association with one or more markers to allow for selection of host cells which contain the construct(s). The constructs can be prepared in conventional ways, where the coding sequences and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc. as appropriate. The construct(s) once completed and demonstrated to have the appropriate sequences may then be introduced into a host cell by any convenient means. The constructs may be incorporated into vectors capable of episomal replication (e.g. BPV or EBV vectors) or into vectors designed for integration into the host cells' chromosomes. The constructs may be integrated and packaged into non-replicating, defective viral genomes like Adenovirus, Adeno-associated virus (AAV), or Herpes simplex virus (HSV) or others, including retroviral vectors, for infection or transduction into cells. Alternatively, the construct may be introduced by protoplast fusion, electroporation, biolistics, calcium Phosphate transfection, lipofection, microinjection of DNA or the like. The host cells will in some cases be grown and expanded in culture before introduction of the construct(s), followed by the appropriate treatment for introduction of the construct(s) and integration of the construct(s). The cells will then be expanded and screened by virtue of a marker present in the constructs. Various markers which may be used successfully include hprt, neomycin resistance, thymidine kinase, hygromycin resistance, etc., and various cell-surface markers such as Tac, CD8, CD3, Thy1 and the NGF receptor.

In some instances, one may have a target site for homologous recombination, where it is desired that a construct be integrated at a particular locus. For example, one can delete and/or replace an endogenous gene (at the same locus or elsewhere) with a recombinant target construct of this invention. For homologous recombination, one may generally use either Omega or O-vectors. See, for example, Thomas and Capecchi, *Cell* (1987) 51, 503–512; Mansour, et al., *Nature* (1988) 336, 348–352; and Joyner, et al., *Nature* (1989) 338, 153–156.

The constructs may be introduced as a single DNA molecule encoding all of the genes, or different DNA molecules having one or more genes. The constructs may be introduced simultaneously or consecutively, each with the same or different markers.

Vectors containing useful elements such as bacterial or yeast origins of replication, selectable and/or amplifiable markers, promoter/enhancer elements for expression in procaryotes or eucaryotes, and mammalian expression control elements, etc. which may be used to prepare stocks of construct DNAs and for carrying out transfections are well known in the art, and many are commercially available.

Introduction of Constructs into Animals

Cells which have been modified ex vivo with the DNA constructs may be grown in culture under selective conditions and cells which are selected as having the desired construct(s) may then be expanded and further analyzed, using, for example, the polymerase chain reaction for determining the presence of the construct in the host cells and/or assays for the production of the desired gene product(s). Once modified host cells have been identified, they may then be used as planned, e.g. grown in culture or introduced into a host organism.

Depending upon the nature of the cells, the cells may be introduced into a host organism, e.g. a mammal, in a wide variety of ways. Hematopoietic cells may be administered by injection into the vascular system, there being usually at least about $10^4$ cells and generally not more than about $10^{10}$ cells. The number of cells which are employed will depend upon a number of circumstances, the purpose for the introduction, the lifetime of the cells, the protocol to be used, for example, the number of administrations, the ability of the cells to multiply, the stability of the therapeutic agent, the physiologic need for the therapeutic agent, and the like. Generally, for myoblasts or fibroblasts for example, the number of cells will be at least about $10^4$ and not more than about $10^9$ and may be applied as a dispersion, generally being injected at or near the site of interest. The cells will usually be in a physiologically-acceptable medium.

Cells engineered in accordance with this invention may also be encapsulated, e.g. using conventional biocompatible materials and methods, prior to implantation into the host organism or patient for the production of a therapeutic protein. See e.g. Hguyen et al, Tissue Implant Systems and Methods for Sustaining viable High Cell Densities within a Host, U.S. Pat. No. 5,314,471 (Baxter International, Inc.); Uludag and Sefton, 1993, J Biomed. Mater. Res. 27(10) :1213–24 (HepG2 cells/hydroxyethyl methacrylate-methyl methacrylate membranes); Chang et al, 1993, Hum Gene Ther 4(4):433–40 (mouse Ltk- cells expressing hGH/ immunoprotective perm-selective alginate microcapsules; Reddy et al, 1993, J Infect Dis 168(4):1082–3 (alginate); Tai and Sun, 1993, FASEB J 7(11):1061–9 (mouse fibroblasts expressing hGH/alginate-poly-L-lysine-alginate membrane); Ao et al, 1995, Transplanataion Proc. 27(6) :3349, 3350 (alginate); Rajotte et al, 1995, Transplantation Proc. 27(6):3389 (alginate); Lakey et al, 1995, Transplantation Proc. 27(6):3266 (alginate); Korbutt et al, 1995, Transplantation Proc. 27(6):3212 (alginate); Dorian et al, U.S. Pat. No. 5,429,821 (alginate); Emerich et al, 1993, Exp Neurol 122(1):37–47 (polymer-encapsulated PC12 cells); Sagen et al, 1993, J Neurosci 13(6):2415–23 (bovine chromaffin cells encapsulated in semipermeable polymer membrane and implanted into rat spinal subarachnoid space); Aebischer et al, 1994, Exp Neurol 126(2):151–8 (polymer-encapsulated rat PC12 cells implanted into monkeys; see also Aebischer, WO 92/19595); Savelkoul et al, 1994, J Immunol Methods 170(2):185–96 (encapsulated hybridomas producing antibodies; encapsulated transfected cell lines expressing various cytokines); Winn et al, 1994, PNAS USA 91(6):2324–8 (engineered BHK cells expressing human nerve growth factor encapsulated in an immunoisolation polymeric device and transplanted into rats); Emerich et al, 1994, Prog Neuropsychopharmacol Biol Psychiatry 18(5):935–46 (polymer-encapsulated PC12 cells implanted into rats); Kordower et al, 1994, PNAS USA 91(23) :10898–902 (polymer-encapsulated engineered BHK cells expressing hNGF implanted into monkeys) and Butler et al WO 95/04521 (encapsulated device). The cells may then be introduced in encapsulated form into an animal host, preferably a mammal and more preferably a human subject in need thereof. Preferably the encapsulating material is semipermeable, permitting release into the host of secreted proteins produced by the encapsulated cells. In many embodiments the semipermeable encapsulation renders the encapsulated cells immunologically isolated from the host organism in which the encapsulated cells are introduced. In those embodiments the cells to be encapsulated may express one or more chimeric proteins containing component domains derived from proteins of the host species and/or from viral proteins or proteins from species other than the host species. For example in such cases the chimeras may contain elements derived from GAL4 and VP16. The cells may be derived from one or more individuals other than the recipient and may be derived from a species other than that of the recipient organism or patient.

Instead of ex vivo modification of the cells, in many situations one may wish to modify cells in vivo. For this purpose, various techniques have been developed for modification of target tissue and cells in vivo. A number of viral vectors have been developed, such as adenovirus, adeno-associated virus, and retroviruses, which allow for transfection and, in some cases, integration of the virus into the host. See, for example, Dubensky et al. (1984) Proc. Natl. Acad. Sci. USA 81, 7529–7533; Kaneda et al., (1939) Science 243,375–378; Hiebert et al. (1989) Proc. Natl. Acad. Sci. USA 86, 3594–3598; Hatzoglu et al. (1990) J. Biol. Chem. 265, 17285–17293 and Ferry, et al. (1991) Proc. Natl. Acad. Sci. USA 88, 8377–8381. The vector may be administered by injection, e.g. intravascuarly or intramuscularly, inhalation, or other parenteral mode. Non-viral delivery methods such as administration of the DNA via complexes with liposomes or by injection, catheter or biolistics may also be used.

In accordance with in vivo genetic modification, the manner of the modification will depend on the nature of the tissue, the efficiency of cellular modification required, the number of opportunities to modify the particular cells, the accessibility of the tissue to the DNA composition to be introduced, and the like. By employing an attenuated or modified retrovirus carrying a target transcriptional initiation region, if desired, one can activate the virus using one of the subject transcription factor constructs, so that the virus may be produced and transfect adjacent cells.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

Applications

This invention is applicable to any situation that calls for expression of an exogenously-introduced gene embedded within a large genome. The desired expression level could be preset very high or very low. The system may be further engineered to achieve regulated or titratable expression. See e.g. PCT/US93/01617. In most cases, the inadvertant activation of unrelated cellular genes is undesirable.

1. Constitutive High-level Gene Expression in Gene Therapy

Gene therapy often requires controlled high-level expression of a therapeutic gene, sometimes in a cell-type specific pattern. By supplying the therapeutic gene with saturating amounts of an activating transcription factor in accordance with this invention, considerably higher levels of gene expression can be obtained relative to natural promoters or enhancers, which are dependent on endogenous transcription factors. Thus, one application of this invention to gene therapy is the delivery of a two-transcription-unit cassette (which may reside on one or two plasmid molecules, depending on the delivery vector) consisting of (1) a transcription unit encoding a transcription factor, whether naturally occurring or designed as described above, for instance comprising a composite DNA-binding domain and a strong transcription activation domain (e.g., derived from the VP16 protein or a human transcription factor) and (2) a transcription unit consisting of the target gene linked to and under the control of a minimal promoter carrying one, and preferably several, binding sites for the composite DNA-binding domain. Cointroduction of the two transcription units into a cell results in the production of the hybrid transcription factor which in turn activates the therapeutic gene to high level. This strategy essentially incorporates an amplification step, because the promoter that would be used to produce the therapeutic gene product in conventional gene therapy is used instead to produce the activating transcription factor. Each transcription factor has the potent al to direct the production of multiple copies of the therapeutic protein.

This method may be employed to increase the efficacy of many gene therapy strategies by substantially elevating the expression of a therapeutic target gene, allowing expression to reach therapeutically effective levels. Examples of therapeutic genes that would benefit from this strategy are genes that encode secreted therapeutic proteins, such as cytokines (e.g., IL-2, IL-4, IL-12), CFTR (see e.g. Grubb et al, 1994, Nature 371:302–6), growth factors (e.g., VEGF), antibodies, and soluble receptors. Other candidate therapeutic genes are disclosed in PCT/US93/01617. This strategy may also be used to increaise the efficacy of "intracellular immunization" agents, molecules like ribozymes, antisense RNA, and dominant-negative proteins, that act either stoichiometrically or by competition. Examples include agents that block infection by or production of HIV or hepatitis virus and agents that antagonize the production of oncogenic proteins in tumors.

It should be appreciated that in practice, the system is subject to many variables, such as the efficiency of expression and, as appropriate, the level of secretion, the activity of the expression product, the particular need of the patient, which may vary with time and circumstances, the rate of loss of the cellular activity as a result of loss of cells or expression activity of individual cells, and the like.

Therefore, it is expected that for each individual patient, even if there were universal cells which could be administered to the population at large, each patient would be monitored for the proper dosage for the individual.

2. Production of Recombinant Proteins

Production of recombinant therapeutic proteins for commercial and investigational purposes is often achieved through the use of mammalian cell lines engineered to express the protein at high level. The use of mammalian cells, rather than bacteria or yeast, is indicated where the Droper function of the protein requires post-translational modifications not generally performed by heterologous cells. Examples of proteins produced commercially this way include erythropoietin, tissue plasminogen activator, clotting factors such as Factor VIII:c, antibodies, etc. The cost of producing proteins in this fashion is directly related to the level of expression achieved in the engineered cells. Thus, because the constitutive two-transcription-unit system described above can achieve considerably higher expression levels than conventional expression systems, it may greatly reduce the cost of protein production.

3. Biological Research

This invention is applicable to a wide range of biological experiments in which precise control over a target gene is desired. These include: (1) expression of a protein or RNA of interest for biochemical purification; (2) tissue or organ specific expression of a protein or RNA of interest in transgenic animals for the purposes of evaluating its biological function. Transgenic animal models and other applications for which this invention may be used include those disclosed in U.S. patent application Ser. Nos. 08/292,595 and 08/292,596 (filed Aug. 18, 1994).

This invention further provides kits useful for the foregoing applications. Such kits contain a first DNA sequence encoding a transcription factor and a second DNA sequence containing a target gene linked to a DNA element to which the transcription factor is capable of binding. Alternatively, the second DNA sequence may contain a cloning site for insertion of a desired target gene by the practitioner.

The following examples contain important additional information, exemplification and guidance which can be adapted to the practice of this invention in its various embodiments and the equivalents thereof. The examples are offered by way illustration and not by way limitation.

EXAMPLES

I. Individual DNA-binding and Transcription Activating Components are Modular, may be Incorporated into Fusion Proteins with Various other Domains and Function as Intended in Cell Culture and in Animals:

A. ZFHD1 and p65 Work Well Individually in Cell Culture and in Whole Animals in Drug-dependent (Regulatable) Transcription Systems 1. Constructs Encoding Chimeric Transcription Factors (a)

Unless otherwise stated, all DNA manipulations described in this and other examples were performed using standard procedures (See e.g., F. M. Ausubel et al., Eds., Current Protocols in Molecular Biology (John Wiley & Sons, New York, 1994).

(b) Plasmids

Constructs encoding fusions of human FKBP12 (hereafter 'FKBP') with the yeast GAL4 DNA binding domain, the HSV VP16 activation domain, human T cell CD3 zeta chain intracellular domain or the intracellular domain of human FAS are disclosed in PCT/US94/01617.

Additional DNA vectors for directing the expression of fusion proteins relevant to this invention were derived from the mammalian expression vector pCGNN (Attar, R. M. and Gilman, M. Z. 1992. MCB 12: 2432–2443). Inserts cloned as XbaI-BamHI fragments into pCGNN are transcribed under the control of the human CMV promoter and enhancer sequences (nucleotides −522 to +72 relative to the cap site), and are expressed with an optional epitope tag (a 16 amino acid portion of the *H. influenzae* hemaglutinin gene that is recognized by the monoclonal antibody 12CA5) and, in the case of transcription factor domains, with an N-terminal nuclear localization sequence (NLS; from SV40 T antigen).

Except where stated, all fragments cloned into pCGNN were inserted as XbaI-BamHI fragments that included a SpeI site just upstream of the BamHI site. As XbaI and SpeI produce compatible ends, this allowed further XbaI-BamHI fragments to be inserted downstream of the initial insert and facilitated stepwise assembly of proteins comprising multiple components. A stop codon was interposed between the SpeI and BamHI sites. For initial constructs, the vector pCGNN-GAL4 was additionally used, in which codons 1–94 of the GAL4 DNA binding domain gene were cloned into the XbaI site of pCGNN such that a XbaI site is regenerated only at the 3' end of the fragment. Thus XbaI-BamHI fragments could be cloned into this vector to generate GAL4 fusions, and subsequently recovered.

(c) Constructs Encoding GAL4 DNA Binding Domain-FRAP Fisions

To obtain portions of the human FRAP gene, human thymus total RNA (Clontech #64028-1) was reverse transcribed using MMLV reverse transcriptase and random hexamer primer (Clontech 1st strand synthesis kit). This cDNA was used directly in a PCR reaction containing primers 1 and 2 and Pfu polymerase (Stratagene). The primers were designed to amplify the coding sequence for amino acids 2025–2113 inclusive of human FRAP: an 89 amino acid region essentially corresponding to the minimal 'FRB' domain identified by Chen et al. (*Proc. Natl. Acad. Sci. USA* (1995) 92, 4947–4951) as necessary and sufficient for FKBP-rapamycin binding (hereafter named FRB). The appropriately-sized band was purified, digested with XbaI and SpeI, and ligated into XbaI-SpeI digested pCGNN-GAL4. This construct was confirmed by restriction analysis (to verify the correct orientation) and DNA sequencing and designated pCGNN-GAL4-1 FRB.

Constructs encoding FRB multimers were obtained by isolating the FRB XbaI-BamHI fragment, and then ligating it back into pCGNN-GAL4-1 FRB digested with SpeI and BamHI to generate pCGNN-GAL4-2FRB, which was confirmed by restriction analysis. This procedure was repeated analogously on the new construct to yield pCGNN-GAL4-3FRB and pCGNN-GAL4-4FRB.

Vectors were also constructed that encode larger fragments of FRAP, encompassing the minimal FRB domain (amino acids 2025–2113) but extending beyond it. PCR primers were designed that amplify various regions of FRAP flanked by 5' XbaI and 3' SpeI sites as indicated below.

| Designation | amino acids | 5' primer | 3' primer |
|---|---|---|---|
| FRAP$_a$ | 2012–2127 | 6 | 7 |
| FRAP$_b$ | 1995–2141 | 5 | 8 |
| FRAP$_c$ | 1945–2113 | 3 | 2 |
| FRAP$_d$ | 1995–2113 | 5 | 2 |
| FRAP$_e$ | 2012–2113 | 6 | 2 |
| FRAP$_f$ | 2025–2127 | 1 | 7 |

-continued

| Designation | amino acids | 5' primer | 3' primer |
|---|---|---|---|
| FRAP$_g$ | 2025–2141 | 1 | 8 |
| FRAP$_h$ | 2025–2174 | 1 | 4 |
| FRAP$_i$ | 1945–2174 | 3 | 4 |

Initially, fragment FRAP$_i$ was amplified by RT-PCR as described above, digested with XbaI and SpeI, and ligated into XbaI-SpeI digested pCGNN-GAL4. This construct, pCGNN-GAL4-FRAP$_i$, was analyzed by PCR to confirm insert orientation and verified by DNA sequencing. It was then used as a PCR substrate to amplify the other fragments using the primers listed. The new fragments were cloned as GAL4 fusions as described above to yield the constructs pCGNN-GAL4-FRAP$_a$, pCGNN-GAL4-FRAP$_b$ etc, which were confirmed by DNA sequencing.

Vectors encoding concatenates of two of the larger FRAP fragments, FRAP$_d$ and FRAPe, were generated by analogous methods to those used earlier. XbaI-BamHI fragments encoding FRAP$_d$ and FRAP$_e$ were isolated from pCGNN-GAL4-FRAP$_d$ and pCGNN-GAL4-FRAP$_e$ and ligated back into the same vectors digested with SpeI and BamHI to generate pCGNN-GAL4-2FRAP$_d$ and pCGNN-GAL4-2FRAP$_e$. This procedure was repeated analogously on the new constructs to yield pCGNN-GAL4-3FRAP$_d$, pCGNN-GAL4-3FRAP$_e$, pCGNN-GAL4-4FRAP$_d$ and pCGNN-GAL4-4FRAP$_e$. All constructs were verified by restriction analysis.

(d) Constructs Encoding FRAP-VP16 Activation Domain Fusions

To generate N-terminal fusions of FRB domain(s) with the activation domain of the Herpes Simplex Virus protein VP16, the XbaI-BamHI fragments encoding 1, 2, 3 and 4 copies of FRB were recovered from the GAL4 fusion vectors and ligated into XbaI-BamHI digested pCGNN to yield pCGNN-1 FRB, pCGNN-2FRB etc. These vectors were then digested with SpeI and BamHI. An XbaI-BamHI fragment encoding eamino acids 414–490 of VP16 was isolated from plasmid pCG-Gal4-VP16 (Das, G., Hinkley, C.S. and Herr, W. (1995) *Nature* 374, 657–660) and ligated into the SpeI-BamHI digested vectors to generate pCGNN-1FRB-VP16, pCGNN-2FRB-VP16, etc. The constructs were verified by restriction analysis and/or DNA sequencing.

(e) Constructs Encoding ZFHD1 DNA Binding Domain-FRAP Fusions

An expression vector for directing the expression of ZFHD1 coding sequence in mammalian cells was prepared as follows. Zif268 sequences were amplified from a cDNA clone by PCR using primers 5'Xba/Zif and 3'Zif+G. Oct1 homeodomain sequences were amplified from a cDNA clone by PCR using primers 5'Not Oct HD and Spe/Bam 3'Oct. The Zif268 PCR fragment was cut with XbaI and NotI. The Oct1 PCR fragment was cut with NotI and BamHI. Both fragments were ligated in a 3-way ligation between the XbaI and BamHI sites of pCGNN (Attar and Gilman, 1992) to make pCGNNZFHD1 in which the cDNA insert is under the transcriptional control of human CMV promoter arid enhancer sequences and is linked to the nuclear localization sequence from SV40 T antigen. The plasmid pCGNN also contains a gene for ampicillin resistance which can serve as a selectable marker. (Derivatives, pCGNNZFHD1-FKBPx1 and pCGNNZFHD1-FKBPx3, were prepared containing one or three tandem repeats of human FKBP12 ligated as an XbaI-BamHI fragment between the Spe1 and BamHI sites of pCGNNZFHD1. A sample of pCGNNZFHD1-FKBPx3 has been deposited with the American Type Culture Collection under ATCC Accession No. 97399.)

and ligated into XbaI-BamHI digested pCGNN to yield the plasmids pCGNN-1 FRAP$_e$, pCGNN-2FRAP$_e$ etc. These vectors were then digested with SpeI and BamHI, and an

```
Primers:
5'Xba/Zif      5'ATGCTCTAGAGAACGCOCATATGCTTGCCCT                    [SEQ ID NO:6]
3'Zif+G            5'ATGCGCGGCCGCCGCCTGTGTGGGTGCGGATGTG             [SEQ ID NO:7]

5'Not OctHD    5'ATGCGCGGCCGCAGGAGGAAGAAACGCACCAGC                  [SEQ ID NO:8]
Spe/Bam 3'Oct 5'GCATGGATCCGATTCAACTAGTGTTGATTCTTTTTTCTTTCTGGCGGCG   [SEQ ID NO:9]
```

To generate C-terminal fusions of FRB domain(s) with the chimeric DNA binding protein ZFHD1, the XbaI-BamHI fragments encoding 1, 2, 3 and 4 copies of FRB were recovered from the GAL4 fusion vectors and ligated into Spe-BamHI digested pCGNN-ZFHD1 to yield pCGNN-ZFHD1-1FRB, pCGNN-ZFHD1-2FRB etc. constructs were verified by restriction analysis and/or DNA sequencing.

To examine the effect of introducing additional 'linker' polypeptide between ZFHD1 and a C-terminal FRB domain, FRAP fragments encoding extra sequence N-terminal to FRB were cloned as ZFHD1 fusions. XbaI-BamHI fragments encoding FRAP$_a$, FRAP$_b$, FRAP$_c$, FRAP$_d$ and FRAP$_e$ were excised from the vectors pCGNN-GAL4-FRAP$_a$, pCGNN-GAL4-FRAP$_b$ etc and ligated into Spel-BamHI digested pCGNN-ZFHD1 to yield the vectors pCGNN-ZFHD1-FRAP$_a$, pCGNN-ZFHD1-FRAP$_b$, etc. Vectors encoding fusions of ZFHD1 to 2, 3 and 4 C-terminal copies of FRAP$_e$ were also constructed by isolating XbaI-BamHI fragments encoding 2FRAP$_e$, 3FRAP$_e$ and 4FRAP$_e$ from pCGNN-GAL4-2FRAP$_e$, pCGNN-GAL4-3FRAP$_e$ and pCGNN-GAL4-4FRAP$_e$ and ligating them into Spel-BamHI digested pCGNN-ZFHD1 to yield the vectors pCGNN-ZFHD1-2FRAP$_e$, pCGNN-ZFHD1-3FRAP$_e$ and pCGNN-ZFHD1-4FRAP$_e$. All constructs were verified by restriction analysis.

XbaI-BamHI fragment encoding ZFHD1 (isolated from pCGNN-ZFHD1) ligated in to yield the constructs pCGNN-1 FRAP$_e$-ZFHD1, pCGNN-2FRAP$_e$-ZFHD1 etc, which were verified by restriction analysis.

(f) Constructs Encoding FRAP-p65 Activation Domain Fusions

To generate fusions of FRB domain(s) with the activation domain of the human NF-kB p65 subunit (hereafter designated p65), two fragments were amplified by PCR from the plasmid pCG-p65. Primers 9 (p65/ 5' Xba) and 11 (p65 3' Spe/Bam) amplify the coding sequence for amino acids 450–550, and primers 10 (p65/1361 Xba) and 11 amplify the coding sequence for amino acids 361–550, both flanked by 5' XbaI and 3' Spel/BamHI sites. PCR products were digested with XbaI and BamHI and cloned into XbaI-BamHI digested pCGNN to yield pCGNN-p65(450–550) and pCGNN-p65(361–550). The constructs were verified by restriction analysis and DNA sequencing.

The 100 amino acid P65 transcription activation sequence is encoded by the following linear sequence:

```
CTGGGGGCCTTGCTTGGCAACAGCACAGACCCAGCTGTGTTCACAGACCTGGCATCCGTCGACAACTCCGAGTTT  [SEQ ID NO:10]

CAGCAGCTGCTGAACCAGGGCATACCTGTGGCCCCCCACACAACTGAGCCCATGCTGATGGAGTACCCTGAGGCT

ATAACTCGCCTAGTGACAGGGGCCGACAGGCCCCCCGACCCAGCTCCTGCTCCACTGGGGGCCCCGGGGCTCCCC

AATGGCCTCCTTTCAGGAGATGAAGACTTCTCCTCCATTGCGGACATGGACTTCTCAGCCCTGCTGAGTCAGATC

AGCTCC
```

Vectors were also constructed that encode N-terminal fusions of FRB domain(s) with ZFHD1. XbaI-BamHI fragments encoding 1, 2, 3 and 4 copies of FRAP$_e$ were isolated from pCGNN-GAL4-1 FRAP$_e$, pCGNN-GAL4-2FRAP$_e$ etc The more extended p65 transcription activation domain (351–550) is encoded by the following linear sequence:

```
CTGGAGTTTCCCACCATGGTGTTTCCTTCTGGGCAGATCAGCCAGGCCTCGGCCTTGGCCCCGGCCCCTCCCCAA  [SEQ ID NO:11]

GTCCTGCCCCAGGCTCCAGCCCCTGCCCCTGCTCCAGCCATGGTATCAGCTCTGGCCCAGGCCCCAGCCCCTGTC

CCAGTCCTAGCCCCAGGCCCTCCTCAGGCTGTGGCCCCACCTGCCCCAAGCCCACCCAGGCTGGGGAAGGAACG

CTGTCAGAGGCCCTGCTGCAGCTGCAGTTTGATGATGAAGACCTGGGGGCCTTGCTTGGCAACAGCACAGACCCA

GCTGTGTTCACAGACCTGGCATCCGTCGACAACTCCGAGTTTCAGCAGCTGCTGAACCAGGGCATACCTGTGGCC

CCCCACACAACTGACCCATGCTGATGCAGTACCCTGAGGCTATAACTCGCCGTAGTGACAGCCCAGAGGCCCCC

GACCCAGCTCCTGCTCCACTGGGGGCCCCGGGGCTCCCCAATGGCCTCCTTTCAGGAGATGAAGACTTCTCCTCC

ATTGCGGAVATGGACTTCTCAGCCCTGCTGAGTCAGATCAGCTCCTAA
```

To generate N-terminal fusions of FRB domain(s) with portions of the p65 activation domain, plasmids pCGNN-1

FRB, pCGNN-2FRB etc were digested with SpeI and BamHI. An XbaI-BamHI fragment encoding p65 (450–550) was isolated from pCGNN-p65(450–550) and ligated into the SpeI-BamHI digested vectors to yield the plasmids pCGNN-1FRB-p65(450–550), pCGNN-2FRB-p65 (450–550) etc. The construct pCGNN-1FRB-p65(361–550) was made similarly using an XbaI-BamHI fragment isolated from pCGNN-p65(361–550). These constructs were verified by restriction analysis.

To examine the effect of introducing additional 'linker' polypeptide between the p65 activation domain and an N-terminal FRB domain, FRAP fragments encoding extra sequence C-terminal to FRB were cloned as p65 fusions. XbaI-BamHI fragments encoding $FRAP_a$, $FRAP_b$, $FRAP_f$, $FRAP_g$ and $FRAP_h$ were excised from the vectors pCGNN-GAL4-$FRAP_a$, pCGNN-GAL4-$FRAP_b$ etc and ligated into XbaI-BamHI digested pCGNN to yield the vectors pCGNN-$FRAP_a$, pCGNN-$FRAP_b$, etc. These plasmids were then digested with SpeI and BamHI, and a XbaI-BamHI fragment encoding p65 (amino acids 450–550) ligated in to yield the five vectors pCGNN-$FRAP_a$-p65, pCGNN-$FRAP_b$-p65, etc, which were verified by restriction analysis.

Vectors encoding fusions of p65 to 1 and 3 N-terminal copies of $FRAP_e$ were also prepared by digesting pCGNN-1 $FRAP_e$ and pCGNN-3$FRAP_e$ with SpeI and BamHI. XbaI-BamHI fragments encoding p65(450–550) and p65 (361–550) (isolated from pCGNN-p65(450–550) and pCGNN-p65(361–550)) were then ligated in to yield the vectors pCGNN-1 $FRAP_e$-p65(450–550), pCGNN-3$FRAP_e$-p65(450–550), pCGNN-1 $FRAP_e$-p65(361–550) and pCGNN-3$FRAP_e$-p65(361–550). All constructs were verified by restriction analysis.

Vectors were also constructed that encode C-terminal fusions of FRB domain(s) with portions of the p65 activation domain. Plasmids pCGNN-p65(450–550) and pCGNN-p65(361–550) were digested with SpeI and BamHI, and XbaI-BamHI fragments encoding 1 and 3 copies of $FRAP_e$ (isolated from pCGNN-GAL4-1 $FRAP_e$ and pCGNN-GAL4-3$FRAP_e$) and 1 copy of FRB (isolated from pCGNN-GAL4-1 FRB) ligated in to yield the plasmids pCGNN-p65 (450–550)-1 $FRAP_e$, pCGNN-p65(450–550)-3$FRAP_e$, pCGNN-p65(361–550)-1 $FRAP_e$, pCGNN-p65(361–550)-3$FRAP_e$, pCGNN-p65(450–550)-1 FRB and pCGNN-p65 (361–550)-1FRB. All constructs were verified by restriction analysis.

(g) Further Constructs

Other constructs can be made analogously with the above procedures, but using alternative portions of the FRAP sequence. For example, primers 12 and 13 are used to amplify the entire coding region of FRAP. Primers 1 and 13, 6 and 13, and 5 and 13, are used to amplify three fragments encompassing the FRB domain and extending through to the C-terminal end of the protein (including the lipid kinase homology domain). These fragments differ by encoding different portions of the protein N-terminal to the FRB domain. In each case, RT-PCR is used as described above to amplify the regions from human thymus RNA, the PCR products are purified, digested with XbaI and SpeI, ligated into XbaI-SpeI digested pCGNN, and verified by restriction analysis and DNA sequencing.

(h) Primer sequences

| | | |
|---|---|---|
| 1 | 5'GCATG<u>TCTAGA</u>GAGATGTGGCATGAAGGCCTGGAAG | [SEQ ID NO:12] |
| 2 | 5'GCATC<u>ACTAGT</u>CTTTGAGATTCGTCGGAACACTGA | [SEQ ID NO:13] |
| 3 | 5'GCACAT<u>TCTAGA</u>ATTGATACGCCCAGACCCTTG | [SEQ ID NO:14] |
| 4 | 5'CGATCA<u>ACTAGT</u>AAGTGTCAATTTCCGGGGCCT | [SEQ ID NO:15] |
| 5 | 5'GCACTA<u>TCTAGA</u>CTGAAGAACATGTGTGAGCACAGC | [SEQ ID NO:16] |
| 6 | 5'GCACTA<u>TCTAGA</u>GTGAGCGAGGAGCFGATCCGAGTG | [SEQ ID NO:17] |
| 7 | 5'CGATCA<u>ACTAGT</u>GGAAACATATTGCAGCTCTAAGGA | [SEQ ID NO:18] |
| 8 | 5'CGATCA<u>ACTAGT</u>TGGCACAGCCAATTCAAGGTCCCG | [SEQ ID NO:19] |
| 9 | 5'ATGC<u>TCTAGA</u>CTGGGGGCCTTGCTTGGCAAC | [SEQ ID NO:20] |
| 10 | 5'ATGC<u>TCTAGA</u>GATGAGTTTCCCACCATGGTG | [SEQ ID NO:21] |
| 11 | 5'GCAT<u>GGATCC</u>GCTCA<u>ACTAGT</u>GGAGCTGATCTGACTCAG | [SEQ ID NO:22] |
| 12 | 5'ATGC<u>TCTAGA</u>CTTGGAACCGGACCTGCCGCC | [SEQ ID NO:23] |
| 13 | 5'GCATC<u>ACTAGT</u>CCAGAAAGGGCACCAGCCAATAT | [SEQ ID NO:24] |

Restriction sites are underlined (XbaI = TCTAGA [SEQ ID NO:25], SpeI = ACGAGT [SEQ ID NO:26] BamHI = GGATCC [SEQ ID NO:27]).

(i) DNA sequence of representative final construct:
pCGNN-ZFHD1-1FRB
12CA5 epitope

```
                      M   A   S   S   Y   P   Y   D   V   P   D
5' gtagaagcgcgt ATG GCT TCT AGC TAT CCT TAT GAC GTG CCT GAC SV40 T NLS
 Y   A   S   L   G   G   P   S   S   P   K   K   K   R   K
TAT GCC AGC CTG GGA GGA CCT TCT AGT CCT AAG AAG AAG AGA AAG
                            (X/S)
            ZFHD1 (5')
 V   S   R   E   R   P   Y   A   C   P   V   F   S   C   D...
GTG TCT AGA GAA CGC CCA TAT GCT TGC CCT GTC GAG TCC TGC GA...
    XbaI [SEQ ID NO:28]

ZFHD1(3')         FRB(5')
...R   I   N   T   R   E   M   W   H   E   G   L   F   E...
...AGA ATC AAC ACT AGA GAG ATG TGG CAT GAA GGC CTG GAA GA..
               (S/X) [SEQ ID NO:30]
        FRB(3')
 R   I   S   K   T   S   Y   *
CGA ATC TCA AAG ACT AGT TAT TAG ggatcctgag
                SpeI            BamHI [SEQ ID NO:32]
```

Non-coding nucleotides are indicated in lower case
(S/X) and (X/S) indicate the result of a ligation event between
the compatible products of digestion with XbaI and SpeI, to
produce a sequence that is cleavable by neither enzyme
*Indicates a stop codon (j) Bicistronic Constructs The internal ribosome entry sequence (IRES) from the encephalomyocarditis virus was amplified by PCR from pWZL-Bleo. The resulting fragment, which was cloned into pBS-SK+ (Stratagene), contains an XbaI site and a stop codon upstream of the IRES sequence and downstream of it, an NcoI site encompassing the ATG followed by SpeI and BamHI sites. To facilitate cloning, the sequence around the initiating ATG of pCGNN-ZFHD1-3FKBP was mutated to an NcoI site and the XbaI site was mutated to a NheI site using the oligonucleotides 5'GAATTCCTAGAAGCGA<u>CCATGG</u>CTTCTAGC-3'  [SEQ ID NO:36]

and

5'GAAGAGAAAGGTGG<u>CTAGC</u>GAACGCCCATAT-3' [SEQ ID NO:35]

respectively. An NcoI-BamHI fragment containing ZFHD1-3FKBP was then cloned downstream of pBS-IRES to create pBS-IRES-ZFHD1-3FKBP. The XbaI-BamHI fragment from this plasmid was next cloned into SpeI/BamHI-cut pCGNN-1FRB-p65(361–550) to create pCGNN-1 FRB-p65 (361–550)-IRES-ZFHD1-3FKBP.

2. Retroviral Vectors for the Expression of Chimeric Proteins

Retroviral vectors used to express transcription factor fusion proteins from stably integrated, low copy genes were derived from pSRaMSVtkNeo (Muller et al., MCB 11:1785–92, 1991) and pSRaMSV(XbaI) (Sawyers et al., J. Exp. Med. 181:307–313, 1995). Unique BamHI sites in both vectors were removed by digesting with BamHI, filling in with Klenow and religating to produce pSMTN2 and pSMTX2, respectively. pSMTN2 expresses the Neo gene from an internal thymidine kinase promoter. A Zeocin gene (Invitrogen) will be cloned as a NheI fragment into a unique XbaI site downstream of an internal thymidine kinase promoter in pSMTX2 to yield pSNTZ. This Zeocin fragment was generated by mutagenizing pZeo/SV (Invitrogen) using the following primers to introduce NheI sites flanking the zeocin coding sequence.

Primer 5'-GCCATGGTGGCTAGCCTATAGTGAG  [SEQ ID NO:36]
1
Primer 5'-GGCGGTGTTGGCTAGCGTCGGTCAG  [SEQ ID NO:37]
2 pSMTN2 contains unique EcoRI and HindIII sites downstream of the LTR. To facilitate cloning of transcription factor fusion proteins synthesized as XbaI-BamHI fragments the following sequence was inserted between the EcoRI and HindIII sites to create pSMTN3:

```
12CA5 epitope
                      M   A   S   S   Y   P   Y   D   V   P   D
5' gaattccagaagcgcgt ATG GCT TCT AGC TAT CCT TAT GAC GTG CCT GAC
   EcoR I SV40 T NLS
 Y   A   S   L   G   G   P   S   S   P   K   K   K   R   K
TAT GCC AGC CTG GGA GGA CCT TCT AGT CCT AAG AAG AAG AGA AAG V
GTG TCT AGA TAT CGA GGA TCC CAA GCT T [SEQ ID NO:38]
    XbaI            BamHI    HindIII
```

The equivalent fragment is inserted into a unique EcoRI site of pSMTZ to create pSMTZ3 with the only difference being that the 3' HindIII site is replaced by an EcoRI site.

pSMTN3 and pSMTZ3 permit chimeric transcription factors to be cloned downstream of the 5' viral LTR as Xbal-BamHI fragments and allow selection for stable integrants by virtue of their ability to confer resistance to the antibiotics 418 or Zeocin respectively.

To generate the retroviral vector SMTN-ZFHD1-3FKBP, pCGNN-ZFHD1-3FKBP was first mutated to add an EcoRI site upstream of the first amino acid of the fusion protein. An EcoRI-BamHI(blunted) fragment was then cloned into EcoRI-HindIII(blunted) pSRaMSVtkNeo (ref. 51) so that ZFHD1-3FKBP was expressed from the retroviral LTR.

3. Rapamycin-dependent Transcriptional Activation

Our previous experiments showed that three copies of FKBP fused either to a Gal4 DNA binding domain or a transcription activation domain activated both the stably integrated or transiently transfected reporter gene more strongly than corresponding fusion proteins containing only one or two FKBP domains. To evaluate this parameter with FRB fusion proteins, effector plasmids containing Gal4 DNA binding domain fused to one or more copies of an FRB domain were co-transfected with a plasmid encoding three FKBP domains and a p65 activation domain (3×FKBP-p65) by transient transfection. The results indicate that in this system, four copies of the FRB domain fused to the Gal4 DNA binding domain activated the stably integrated reporter gene more strongly than other corresponding fusion proteins with fewer FRB domains.

Method: HT1080 B cells were grown in MEM supplemented with 10% Bovine Calf Serum. Approximately $4\times10^5$ cells/well in a 6 well plate (Falcon) were transiently transfected by Lipofection procedure as recommended by the supplier (GIBCO, BRL). The DNA: Lipofectamine ratio used in this experiment correspond to 1:6. Cells in each well recieved 500 ng of pCGNN F3-p65, 1.9 ug of PUC 118 plasmid as carrier and 100 ng of one of the following plasmids: pCGNN Gal4-1 FRB, pCGNN Gal4-2FRB, pCGNN Gal4-3FRB or pCGNN Gal4-4FRB. Following transfection, 2 ml fresh media was added and supplemented with Rapamycin to the indicated concentration. After 24 hrs, 100 ul of the media was assayed for SEAP activity as described (Spencer et al, 1993).

To test whether multiple FRB domains fused to a p65 activation domain results in increased transcriptional activation of the reporter gene, we co-transfected HT1080 B cells with plasmids expressing Gal4-3FKBP and 1, 2, 3 or 4 copies of FRB fused to p65 activation domain. Surprisingly, unlike the DNA binding domain-FRB fusions, a single copy of FRB fused to p65 activation domain activated the reporter gene significantly more strongly than corresponding fusion proteins containing 2 or more copies of FRB.

Method: HT1080 B cells were grown in MEM supplemented with 10% Bovine Calf Serum. Approximately $4\times10^5$ cells/well in a 6 well plate were transiently transfected by Lipofection procedure as recommended by GIBCO, BRL. The DNA: Lipofectamine ratio used correspond to 1:6. Cells in each well recieved 1.9 ug of PUC 118 plasmid as carrier, 100 ng of pCGNNGal4F3 and 500 ng one of the following plasmids :pCGNN1, 2, 3 or 4 FRB-p65. Following transfection, 2 ml fresh media was added and supplemented with Rapamycin to the indicated concentration. After 24 hrs, 100 ul of the media was assayed for SEAP activity as described (Spencer et al, 1993).

Similar experiments were also conducted using another stable cell line (HT1080 B14) containing the 5×Gal4-IL2-SEAP reporter gene and DNA sequences encoding a fusion protein containing a Gal4 DNA binding domain and 3 copies of FKBP stably integrated. These cells were transiently transfected with effector plasmids expressing p65 activation domain fused to 1 or more copies of an FRB domain. Similar to our observations with HT1080 B cells, effector plasmids expressing a single copy of FRB-p65 activation domain fusion protein activated the reporter gene more strongly than others; with 2 or more copies of FRB.

4. Rapamycin-dependent Transcriptional Activation in Transiently Transfected Cells: ZFHD1 and p65 Fusions Human fibrosarcoma cells transiently transfected with a SEAP target gene and plasmids encoding representative ZFHD-FKBP- and FRB-p35-containing fusion proteins exhibited rapamycin-dependent and dose-responsive secretion of SEAP into the cell culture medium. SEAP production was not detected in cells in which one or both of the transcription factor fusion plasmids was omitted, nor was it detected in the absence of added rapamycin. When all components were present, however, SEAP secretion was detectable at rapamycin concentrations as low as 0.5 nM. Peak SEAP secretion was observed at 5 nM. Similar results have been obtained when the same transcription factors were used to drive rapamycin-dependent activation of an hGH reporter gene or a stably integrated version of the SEAP reporter gene made by infection with a retroviral vector. It is difficult to determine the fold activation in response to rapamycin since levels of SEAP secretion in the absence of drug are undetectable, but it is clear that in this system there is at least a 1000-fold enhancement over background levels in the absence of rapamycin. Thus, this system exhibits undetectable background activity and high dynamic ange.

Several different configurations for transcription factor fusion proteins were explored. When various numbers of copies of FKBP domains were fused to ZFHD1 and various numbers of copies of FRBs to p65, optimal levels of rapamycin-induced activation ocurred when there were multiple FKBPs fused to ZFHD1 and fewer FRBs fused to p65. The preference for multiple drug-binding domains on the DNA-binding protein may reflect the capacity of these proteins to recruit multiple activation domains and therefore to elicit higher levels of promoter activity. The presence of only 1 drug-binding domain on the activation domain should allow each FKBP on ZFHD to recruit one p65. Any increase in the number of FRBs on p65 would increase the chance that fewer activation domains would be recruited to ZFHD, each one linked my multiple FRB-FKBP interactions.

Methods

HT1080 cells (ATCC CCL-121), derived from a human fibrosarcoma, were grown in MEM supplemented with non-essential amino acids and 10% Fetal Bovine Serum. Cells plated in 24-well dishes (Falcon, $6\times10^4$ cells/well) were transfected using Lipofectamine under conditions recommended by the manufacturer (GIBCO/BRL). A total of 300 ng of the following DNA was transfected into each well: 100 ng ZFHDx12-CMV-SEAP reporter gene, 2.5 ng pCGNN-ZFHD1-3FKBP or other DNA binding domain fusion, 5 ng pCGNN-1FRB-p65(361–550) or other activation domain fusion and 192.5 ng pUC118. In cases where the DNA binding domain or activation domain were omitted an equivalent amount of empty pCGNN expression vector was substituted. Following lipofection (for 5 hours) 500 µl medium containing the indicated amounts of rapamycin was added to each well. After 24 hours, medium was removed and assayed for SEAP activity as described (Spencer et al, Science 262:1019–24, 1993) using a Luminescence Spectrometer (Perkin Elmer) at 350 nm excitation and 450 nm emission. Background SEAP activity, measured from mock-transfected cells, was subtracted from each value.

To prepare transiently transfected HT1080 cells for injection into mice (See below), cells in 100 mm dishes ($2 \times 10^6$ cells/dish) were transfected by calcium phosphate precipitation for 16 hours (Gatz, C., Kaiser, A. & Wendenburg, R., 1991, *Mol. Gen. Genet.* 227, 229–237) with the following DNAs: 10 mg of ZHWTx12-CMV-hGH, 1 mg pCGNN-ZFHD1-3FKBP, 2 mg pCGNN-1FRB-p65(361–550) and 7 mg pUC118. Transfected cells were rinsed 2 times with phosphate buffered saline (PBS) and given fresh medium for 5 hours. To harvest for injection, cells were removed from the dish in Hepes Buffered Saline Solution containing 10 mM EDTA, washed with PBS/0.1% BSA/0.1% glucose and resuspended in the same at a concentration of $2 \times 10^7$ cells/ml.

Plasmids

Construction of the transcription factor fusion plasmids is described above.

pZHWTx12-CMV-SEAP

This reporter gene, containing 12 tandem copies of a ZFHD1 binding site (Pomerantz et al., 1995) and a basal promoter from the immediate early gene of human cytomegalovirus (Boshart et. al., 1985) driving expression of a gene encoding secreted alkaline phosphatase (SEAP), was prepared by replacing the NheI-HindIII fragment of pSEAP Promoter (Clontech) with the following NheI-XbaI fragment containing 12 ZFHD binding sites:

```
GCTAGCTAATGATGGGCGCTCGAGTAATGATGGGCGGTCGACTAATGATGGGCGCTCGAGTAATGATGGGCGTCT [SEQ ID NO:40]

AGCTAATGATGGGCGCTCGAGTAATGATGGGCGGTCGACTAATGATGGGCGCTCGAGTAATGATGGGCGTCTAGC

TAATGATGGGCGCTCGAGTAATGATGGGCGGTCGACTAATGATGGGCGCTCGAGTAATGATGGGCGTCTAGA
```

(the ZFHD1 binding sites are underlined), and the following XbaI-HindIII fragment containing a minimal CMV promoter (−54 to +45):

```
TCTAGAACGCGAATTCCGGTAGGCGTGTACGGTGGGAGGTCTATATAAGCAGAGCTCGTTTAGTGAACCGTCAGA [SEQ ID NO:41]

TCGCCTGGAGACGCCATCCACGCTGTTTTGACCTCCATAGAAGCTT
```

(the CMV minimal promoter is underlined).

pZHWTx12-CMV-hGH

Activation of this reporter gene leads to the production of hGH. It was constructed by replacing the HindIII-BamHI (blunted) fragment of pZHWTx12-CMV-SEAP (containing the SEAP coding sequence) with a HindIII (blunted) -EcoRI fragment from pOGH (containing an hGH genomic clone; Selden et al., MCB 6:3171–3179, 1986; the BamHI and EcoRI sites were blunted together).

pZHWTx12-IL2-SEAP

This reporter gene is identical to pZHWTx12-CMV-SEAP except the XbaI-HindIII fragment containing the minimal CMV promoter was replaced with the following XbaI-HindIII fragment containing a minimal IL2 gene promoter (−72 to +45 with respect to the start site; Siebenlist et al., MCB 6:3042–3049, 1986):

```
TCTAGAACGCGAATTCAACATTTTGACACCCCCATAATATTTTTCCAGAATTAACAGTATAAATTGCATCTCTTG [SEQ ID NO:42]

TTCAAGAGTTCCCTATCACTCTCTTTAATCACTACTCACAGTAACCTCAACTCCTGCCACAAGCTT
```

(the IL2 minimal promoter is underlined).

pLH

To facilitate the stable integration of a single, or few, copies of reporter gene the following retroviral vector was constructed. pLH (LTR-hph), which contains the hygromycin B resistance gene driven by the Moloney murine leukemia virus LTR and a unique internal ClaI site, was constructed as follows: The hph gene was cloned as a HindIII-ClaI fragment from pBabe Hygro (Morganstern and Land, NAR 18:3587–96, 1990) into BamHI-ClaI cut pBabe Bleo (resulting in the loss of the bleo gene; the BamHI and HindIII sites were blunted together).

pLH-ZHWTx12-IL2-SEAP

To clone a copy of the reporter gene containing 12 tandem copies of the ZFHD1 binding site and a basal promoter from the IL2 gene driving expression of the SEAP gene into the pLH retroviral vector, the MluI-ClaI fragment from pZHWTx12-IL2-SEAP (with ClaI linkers added) was cloned into the ClaI site of pLH. It was oriented such that the directions of transcription from the viral LTR and the internal ZFHD-IL2 promoters were the same.

pLH-G5- IL2-SEAP

To construct a retroviral vector containing 5 Gal4 sites embedded in a minimal IL2 promoter driving expression of the SEAP gene, a ClaI-BstBI fragment consisting of the following was inserted into the ClaI site of pLH such that the directions of transcription from the viral LTR and the internal Gal4-IL2 promoters were) the same: A ClaI-HindIII fragment containing 5 Gal4 sites (underlined) and regions −324 to −294 (bold) and −72 to +45 of the IL2 gene (italics)

```
5'ATCGATGTTTTCTGAGTTACTTTTGTATCCCCACCCCCCCTCGAGCTTGCATQCCTG            [SEQ ID NO:43]

CAQQTCGGAGTACTGTCCTCCGAGCGGAGTACTGTCCTCCGAGCGGAGTACTGTCCTCCGAGCG

GAGTACTGTCCTCCGAGCGGAGTACTGTCCTCCGAG CGCAGACTCTAGAGGATCCGAGAACATT

TTGACACCCCCATAATATTTTTCCAGAATTAACAGTATAAATTGCATCTCTTGTTCAAGAGTTC

CCTATCACTCTCTTTAATCACTACTCACAGTAACCTCAACTCCTGCCACAAGCTT.
``` and a HindIII-BstB1 fragment containing the SEAP gene coding sequence (Berger et al., Gene 66:1–10, 1988) mutagenized to add the following sequence (containing a BstB1 site) immediately after the stop codon: [SEQ ID NO:44]

```
    5'-CCCGTGGTCCCGCGTTGCTTCGAT    [SEQ ID NO: 44]
```

5. Rapamycin-dependent Transcriptional Activation in Stably Transfected Cells

We conducted the following experiments to confirm that this system exhibits similar properties in stably transfected cells. We generated stable cell lines by sequential transfection of a SEAP target gene and expression vectors for ZFHD1-3FKBP and 1FRB-p65, respectively. A pool of several dozen stable clones resulting from the final transfection exhibited rapamycin-dependent SEAP production. From this pool, we characterized several individual clones, many of which produced high levels of SEAP in response to rapamycin. One such clone produced SEAP at levels approximately forty times higher than the pool and significantly higher than transiently transfected cells. In an attempt to rigorously quantitate background SEAP production and induction ratio in this clone, we performed a second set of assays in which the length of the SEAP assay was increased by a factor of approximately 50 to detect any SEAP activity in untreated cells. Under these conditions, mock transfected cells produced 47 arbitrary fluorescence units, while the transfected clone produced 54 units in the absence of rapamycin and over 90,000 units at 100 nM rapamycin. Thus, in this stable cell line, background gene expression was negligible and the induction ratio (7 units to 90,000 units) was greater than four orders of magnitude.

To simplify the task of stable transfection, we used a bicistronic expression vector that directs the production of both ZFHD1-3FKBP and 1 FRB-p65 through the use of an internal ribosome entry sequence (IRES). This expression plasmid was cotransfected, together with a zeocin-resistance marker plasmid, into a cell line carrying a retrovirally-transduced SEAP reporter gene, and a pool of approximately fifty drug-resistant clones was selected and expanded. This pool of clones also exhibited rapamycin-dependent SEAP production with no detectable background and a very similar dose-response curve to that observed in transiently transfected cells. Our results indicate that rapamycin-responsive gene expression can be readily obtained in both transiently and stably transfected cells. In both cases, regulation is characterized by very low background and high induction ratios.

Stable cell lines. Helper-free retroviruses containing the reporter gene or DNA binding domain fusion were generated by transient co-transfection of 293T cells (Pear, W. S., Nolan, G. P., Scott, M. L. & Baltimore D., 1993, Production of high-titer helper-free retroviruses by transient transfection. Proc. Natl. Acad. Sci. USA 90, 8392–8396) with a Psi(-) amphotropic packaging vector and the retroviral vectors pLH-ZHWTx12-lL2-SEAP or SMTN-ZFHD1-3FKBP, respectively. To generate a clonal cell line containing the reporter gene stably integrated, HT1080 cells infected with retroviral stock were diluted and selected in the presence of 300 mg/ml Hygromycin B. Individual clones from this and other cell lines described below were screened by transient transfection of the missing components followed by the addition of rapamycin as described above. All 12 clones analyzed were inducible and had little or no basal activity. The most responsive clone, HT1080L, was selected for further study.

HT20-6 cells, which contain the pLH-ZHWTx12-IL2-SEAP reporter gene, ZFHD1-3FKBP DNA binding domain and 1FRB-p65(361–550) activation domain stably integrated, were generated by first infecting HT1080L cells with SMTN-ZFHD1-3FKBP-packaged retrovirus and selecting in medium containing 500 mg/ml G418. A strongly responsive clone, HT1080L3, was then transfected with linearized pCGNN-1FRB-p65(361–550) and pZeoSV (Invitrogen) and selected in medium containing 250 mg/ml Zeocin. Individual clones were first tested for the presence of 1FRB-p65(361–550) by western. Eight positive clones were analyzed by addition of rapamycin. All eight had low basal activity and in six of them, gene expression was induced by at least two orders of magnitude. The clone that gave the strongest response, HT20-6, was selected for further analysis.

HT23 cells were generated by co-transfecting HT1030L cells with linearized pCGNN-1FRB-p65(361–550)-IRES-ZFHD1-3FKBP and pZeoSV and selecting in medium containing 250 mg/ml Zeocin. Approximately 50 clones were pooled for analysis.

For analysis, cells were plated in 96-well dishes ($1.5 \times 10^4$ cells/well) and 200 $\mu$l medium containing the indicated amounts of rapamycin (or vehicle) was added to each well. After 18 hours, medium was removed and assayed for SEAP activity. In some cases, medium was diluted before analysis and relative SEAP units obtained multiplied by the fold-dilution. Background SEAP activity, measured from untransfected HT1080 cells, was subtracted from each value.

6. Rapamycin-dependent Production of hGH in Mice

In Vivo Methods: Animals, husbandry, and general procedures. Male nu/nu mice were obtained from Charles River Laboratories (Wilmington, Mass.) and allowed to acclimate for five days prior to experimentation. They were housed under sterile conditions, were allowed free access to sterile food and sterile water throughout the entire experiment, and were handled with sterile techniques throughout. No immunocompromised animal demonstrated outward infection or appeared ill as a result of housing, husbandry techniques, or experimental techniques.

To transplant transiently transfected cells into mice, $2\times10^6$ transfected HT1080 cells, were suspended in 100 ml PBS/0.1% BSA/0.1% glucose buffer, and administered into four intramuscular sites (approximately 25 ml per site) on the haunches and flanks of the animals. Control mice received equivalent volume injections of buffer alone.

Rapamycin was formulated for in vivo administration by dissolution in equal parts of N,N-dimethylacetamide and a 9:1 (v:v) mixture of polyethylene glycol (average molecular weight of 400) and polyoxyethylene sorbitan monooleate. Concentrations of rapamycin, in the completed formulation, were sufficient to allow for in vivo administration of the appropriate dose in a 2.0 ml/kg injection volume. The accuracy of the dosing solutions was confirmed by HPLC analysis prior to intravenous administration into the tail veins. Some control mice, bearing no transfected HT1080 cells, received 10.0 mg/kg rapamycin. In addition, other control mice, bearing transfected cells, received only the rapamycin vehicle.

Blood was collected by either anesthetizing or sacrificing mice via $CO_2$ inhalation. Anesthetized mice were used to collect 100 ml of blood by cardiac puncture. The mice were revived and allowed to recover for subsequent blood collections. Sacrificed mice were immediately exsanguinated. Blood samples were allowed to clot for 24 hours, at 4° C., and sera were collected following centrifugation at 1000×g for 15 minutes. Serum hGH was measured by the Boehringer Mannheim non-isotopic sandwich ELISA (Cat No. 1 585 878). The assay had a lower detection limit of 0.0125 ng/ml and a dynamic range that extended to 0.4 ng/ml. Recommended assay instructions were followed. Absorbance was read at 405 nm with a 490 nm reference wavelength on a Molecular Devices microtiter plate reader. The antibody reagents in the ELISA demonstrate no cross reactivity with endogenous, murine hGH in diluent sera or native samples.

hGH expression In Vivo. For the assessment of dose-dependent rapamycin-induced stimulation of hGH expression, rapamycin was administered to mice approximately one hour following injection of HT1080 cells. Rapamycin doses were either 0.01, 0.03, 0.1, 0.3, 1.0, 3.0, or 10.0 mg/kg. Seventeen hours following rapamycin administration, the mice were sacrificed for blood collection.

To address the time course of in vivo hGH expression, mice received 10.0 mg/kg of rapamycin one hour following injection of the cells. Mice were sacrificed at 4, 8, 17, 24, and 42 hours following rapamycin administration.

The ability of rapamycin to induce sustained expression of hGH from transplanted HT1080 cells was tested by repeatedly administering rapamycin. Mice were administered transfected HT1080 cells as described above. Approximately one hour following injection of the cells, mice received the first of five intravenous 10.0 mg/kg doses of rapamycin. The four remaining doses were given under anesthesia, immediately subsequent to blood collection, at 16, 32, 48, and 64 hours. Additional blood collections were also performed at 72, 80, 88, and 96 hours following the first rapamycin dose. Control mice were administered cells, but received only vehicle at the various times of administration of rapamycin. Experimental animals and their control counterparts were each assigned to one of two groups. Each of the two experimental groups and two control groups received identical drug or vehicle treatments, respectively. The groups differed in that blood collection times were alternated between the two groups to reduce the frequency of blood collection for each animal.

Results

Rapamycin elicited dose-responsive production of KGH in these animals (FIG. 1). hGH concentrations in the rapamycin-treated animals compared favorably with normal circulating levels in humans (0.2–0.3 ng/ml). No plateau in hGH production was observed in these experiments, suggesting that the maximal capacity of the transfected cells for hGH production was not reached. Control animals—those that received transfected cells but no rapamycin and those that received rapamycin but no cells—exhibited no detectable serum hGH. Thus, the production of hGH in these animals was absolutely dependent upon the presence of both engineered cells and rapamycin.

The presence of significant levels of hGH in the serum 17 hours after rapamycin administration was noteworthy, because hGH is cleared from the circulation with a half-life of less than four minutes in these animals. This observation suggested that the engineered cells continued to secrete hGH for many hours following rapamycin treatment. To examine the kinetics of rapamycin control of hGH production, we treated animals with a single dose of rapamycin and then measured hGH levels at different times thereafter. Serum hGH was observed within four hours of rapamycin treatment, peaked at eight hours (at over one hundred times the sensitivity limit of the hGH ELISA), and remained detectable 42 hours after treatment. hGH concentration decayed from its peak with a half-life of approximately 11 hours. This half-life is several hundredfold longer than the half-life of hGH itself and approximately twice the half-life of rapamycin (4.6 hr) in these animals. The slower decay of serum hGH relative to rapamycin could reflect the presence of higher tissue concentrations of rapamycin in the vicinity of the implanted cells. Alternatively, persistence of hGH production from the engineered cells may be enhanced by the stability of hGH mRNA.

Interestingly, administration of a second dose of rapamycin to these animals at 42 hr resulted in a second peak of serum hGH, which decayed with similar kinetics indicating that the engineered cells retained the ability to respond to rapamycin for at least two days. Therefore, to ascertain the ability of this system to elevate and maintain circulating hGH concentrations, we performed an experiment in which animals received multiple doses of rapamycin at 16-hour intervals. This interval corresponds to the time required for hGH levels to peak and then decline approximately halfway. According to this regimen, rapamycin concentration is predicted to approach a steady-state trough concentration of 1.7 μg/ml after two doses. hGH levels should also approach a steady state trough concentration following the second dose. Indeed, treated animals held relatively stable levels of circulating hGH in response to repeated doses of rapamycin. After the final dose, hGH levels remained constant for 16 hours and then declined with a similar half-life as rapamycin (6.8 hours for hGH versus 4.6 hours for rapamycin). These data suggest that upon multiple dosing, circulating rapamycin imparts tight control over the secretion of hGH from transfected cells in vivo. In particular, it is apparent that protein production is rapidly terminated upon withdrawal of drug.

Discussion

These experiments demonstrate that the transcription factor component modules function appropriately with corresponding target gene constructs in cell culture and in whole animals in a regulatable system.

B. Hybrid Transcription Factors Containing such Modular Components Work Well in Constitutive Expression Plasmids pCGNNZFHD1

An expression vector for directing the expression of ZFHD1 coding sequence in mammalian cells was prepared as follows. Zif268 sequences were amplified from a cDNA clone by PCR using primers 5'Xba/Zif and 3'Zif+G. Oct1 homeodomain sequences were amplified from a cDNA clone by PCR using primers 5'Not Oct HD and Spe/Bam 3'Oct. The Zif268 PCR fragment was cut with XbaI and NotI. The Oct1 PCR fragment was cut with NotI and BamHI. Both fragments were ligated in a 3-way ligation between the XbaI and BamHI sites of pCGNN (Attar and Gilman, 1992) to make pCGNNZFHD1 in which the cDNA insert is under the transcriptional control of human CMV promoter and enhancer sequences and is linked to the nuclear localization sequence from SV40 T antigen. The plasmid pCGNN also contains a gene for ampicillin resistance which can serve as a selectable marker.

pCGNNZFHD1 -p65

An expression vector for directing the expression in mammalian cells of a chimeric transcription factor containing the composite DNA-binding domain, ZFHD1, and a transcription activation domain from p65 (human) was prepared as follows. The sequence encoding the C-terminal region of p65 containing the activation domain (amino acid residues 450–550) was amplified from pCGN-p65 using primers p65 5' Xba and p65 3' Spe/Bam. The PCR fragment was digested with Xba1 and BamH1 and ligated between the the Spe1 and BamH1 sites of pCGNN ZFHD1 to form pCGNN ZFHD-p65AD.

The P65 transcription activation sequence contains the following linear sequence:

pCGNNZFHD1 -FKBPx3

An expression vector for directing the expression of ZFHD1 linked to three tandem repeats of human FKBP was prepared as follows. Three tandem repeats of human FKBP were isolated as an XbaI-BamHI fragment from pCGNNF3 and ligated between the Spe1 and BamHI sites of pCGNNZFHD1 to make pCGNNZFHD1-FKBPx3 (ATCC Accession No. 97399).

pZHVWTx8SVSEAP

A reporter gene construct containing eight tandem copies of a ZFHD1 binding site (Pomerantz et al., 1995) and a gene encoding secreted alkaline phosphatase (SEAP) was prepared by ligating the tandem ZFHD1 binding sites between the Nhe1 and BgIII sites of pSEAP-Promoter Vector (Clontech) to form pZHWTx8SVSEAP. The ZHWTx8SEAP reporter contains two copies of the following sequence in tandem:

```
CTAGCTAATGATGGGOGCTOGAGTAATGATGGGOGGTOGACAATGATGGGOGCTOGAGTAATGATGGGOGT   [SEQ ID NO: 46]
```

The ZFHD1 binding sites are underlined. ps pCGNN F1 and F2

One or two copies of FKBP12 were amplified from pNF3VE using primers FKBP 5' Xba and FKBP 3' Spe/Bam. The PCR fragments were digested with Xba1 and BamH1 and ligated between the Xba1 and BamH1 sites of pCGNN vector to make pCGNN F1 or pPCGNN F2. pCGNNZFHD1-FKBPx3 can serve as an alternate source of the FKBP cDNA.

pCGNN F3

A fragment containing two tandem copies of FKBP was excised from pCGNN F2 by digesting with Xba1 and BamH1. This fragment was ligated between the Spe1 and BamH1 sites of pCGNN F1.

pCGNN F3VP16

The C-terminal region of the Herpes Simplex Virus protein, VP16 (AA 418–490) containing the activation domain was amplified from pCG-Gal4-VP16 using primers VP16 5' Xba and VP16 3' Spe/Bam. The PCR fragment was digested with Xba1 and BamH1 and ligated between the Spe1 and BamH1 sites of pCGNN F3 plasmid.

pCGNN F3p65

The Xba1 and BamH1 fragment of p65 containing the activation domain was prepared as described above. This fragment was ligated between the Spe1 and BamH1 sites of pCGNN F3.

```
CTGGGGGCCTTGCTTGGCAACAGCACAGACCCAGCTGTGTTCACAGACCTGGCATCCGT [SEQ ID NO: 45]

CGACAACTCCGAGTTTCAGCAGCTGCTGAACCAGGGCATACCTGTGGCCCCCCACACAA

CTGAGCCCATGCTGATGGAGTACCCTGAGGCTATAACTCGCCTAGTGACAGGGGCCCAG

AGGCCCCCCGACCCAGCTCCTGCTCCACTGGGGGCCCCGGGGCTCCCCAATGGCCTCCT

TTCAGGAGATGAAGACTTCTCCTCCATTGCGGACATGGACTTCTCAGCCCTGCTGAGTC

AGATCAGCTCC
```

| Primers | | |
|---|---|---|
| 5'Xba/Zif | 5'ATGCTCTAGAGAACGCCCATATGCTTGCCCT | [SEQ ID NO: 47] |
| 3'Zif+G | 5'ATGCGCGGCOGCOGCOGCTGTGTGGGTGCGGATGTG | [SEQ ID NO: 48] |
| 5'Not OctHD | 5'ATGCGCGGCOGCAGGAGGAAGAAAOGCAOOAGC | [SEQ ID NO: 49] |
| Spe/Bam 3'Oct | 5'GCATGGATCCGATTCAACTAGTGTTGATTCTTTTTTCTTTCTGGCGGCG | [SEQ ID NO: 80] |
| FKBP 5'Xba | 5'TCAGTCTAGAGGAGTGCAGGTGGAAACCAT | [SEQ ID NO: 51] |
| FKBP 3'Spe/Bam | 5'TCAGGGATCCTCAATAACTAGTTTCCAGAAGCTC | [SEQ ID NO: 52] |
| VP16 5'Xba | 5'ACTGTCTAGAGTCAGCCTGGGGACGAG | [SEQ ID NO: 153] |
| VP16 3'Spe/Bam | 5'GCATGGATCCGATTCAACTAGTCCCACCGTACTCGTCAATTCC | [SEQ ID NO: 54] |
| P65 5' Xba | 5'ATGCTCTAGACTGGGGGCCTTGCTTGGCAAC | [SEQ ID NO: 55] |
| p65 3' Spe/Bam | 5'GCATGGATCCGCTCAACTAGTGGAGCTGATCTGACTCAG | [SEQ ID NO 56] |

References

1. Attar, R. M., and M. Z. Gilman 1992. *Mol. Cell. Biol.* 12:2432–2443
2. Ausubel, F. M. et al., Eds., 1994. CURRENT PROTOCOLS IN MOLECULAR BIOLOGY (Wiley, N.Y.)
3. Pomerantz, J. L., et al. 1995. Science. 267:93–96.
4. Spencer, D. M., et al. 1993. Science. 262:1019–1024.

II. Evaluation of Representative Illustrative Chimeric Transcription Factors

Constructs

Figure 2:
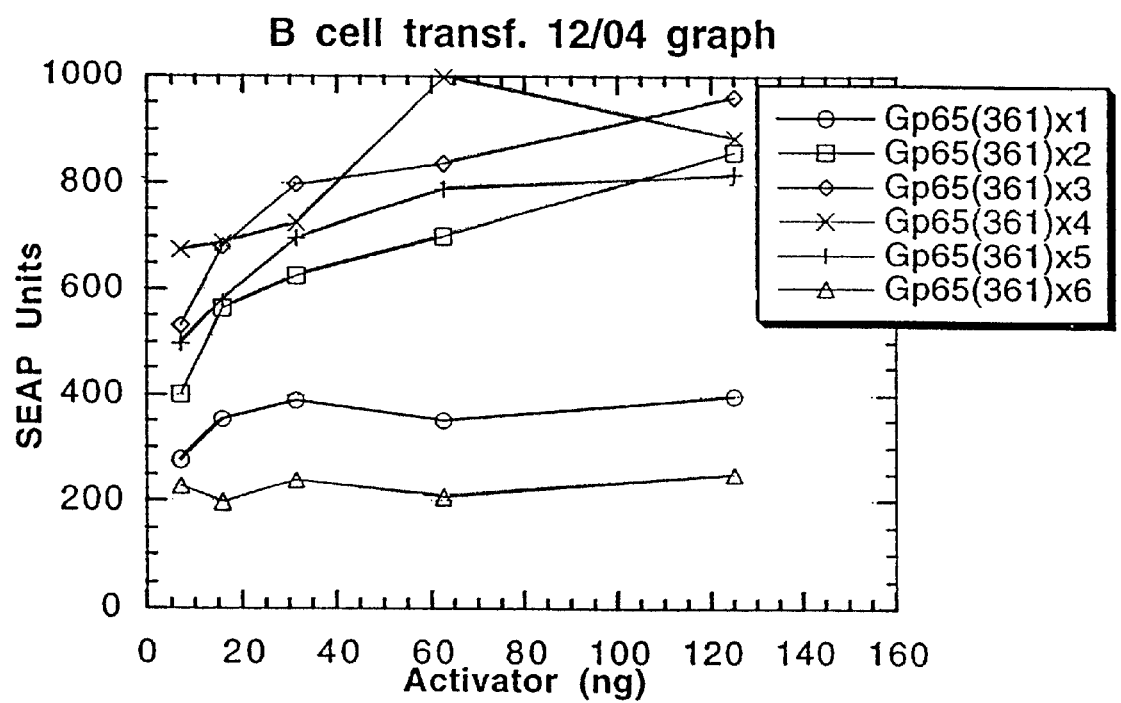
FIGS. 2 through 7 present comparative data on a representative collection of chimeric transcription factors assayed in cell lines into which target gene constructs (SEAP) had been stably integrated as described in the examples which follow below.
Figure 3:
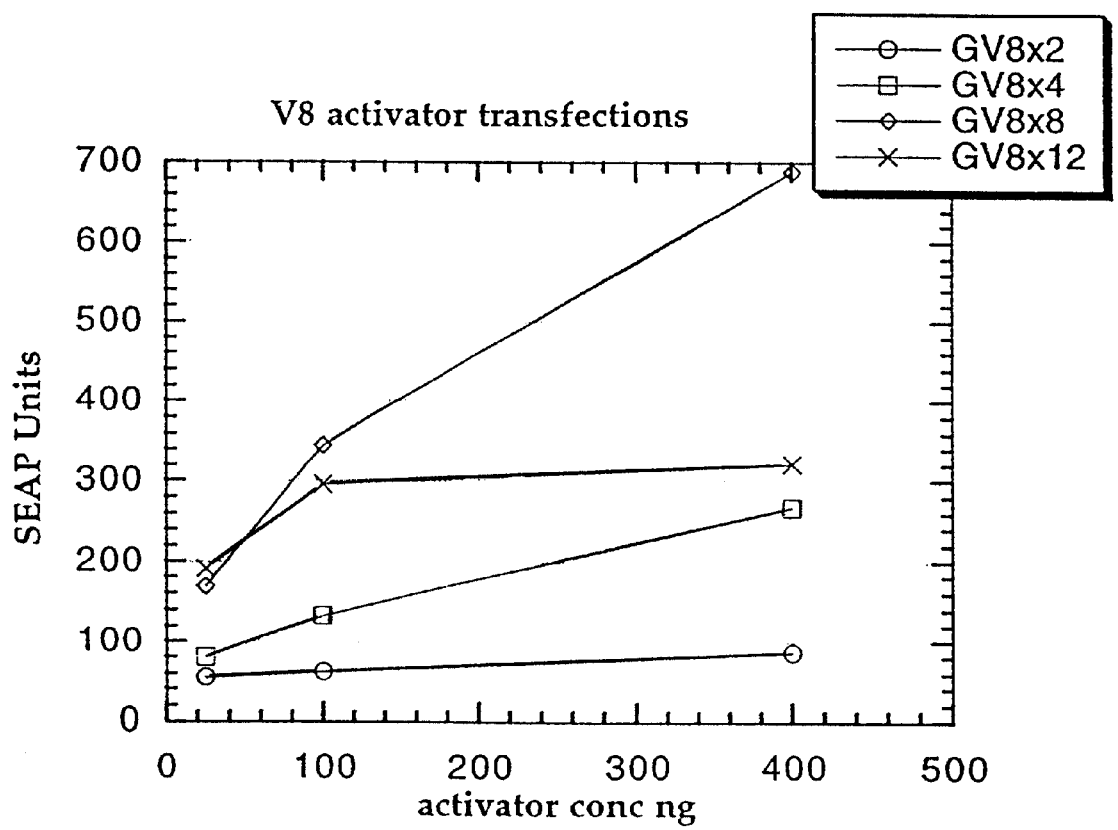
Figure 4:
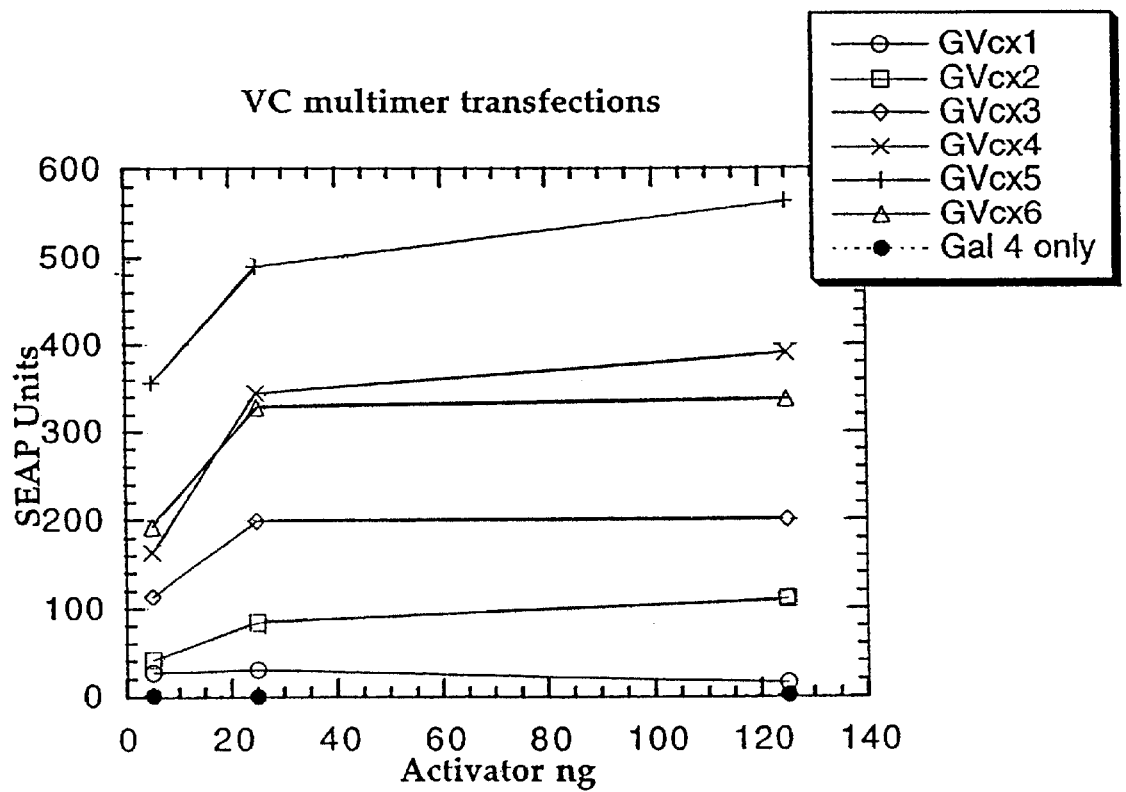
Figure 5:
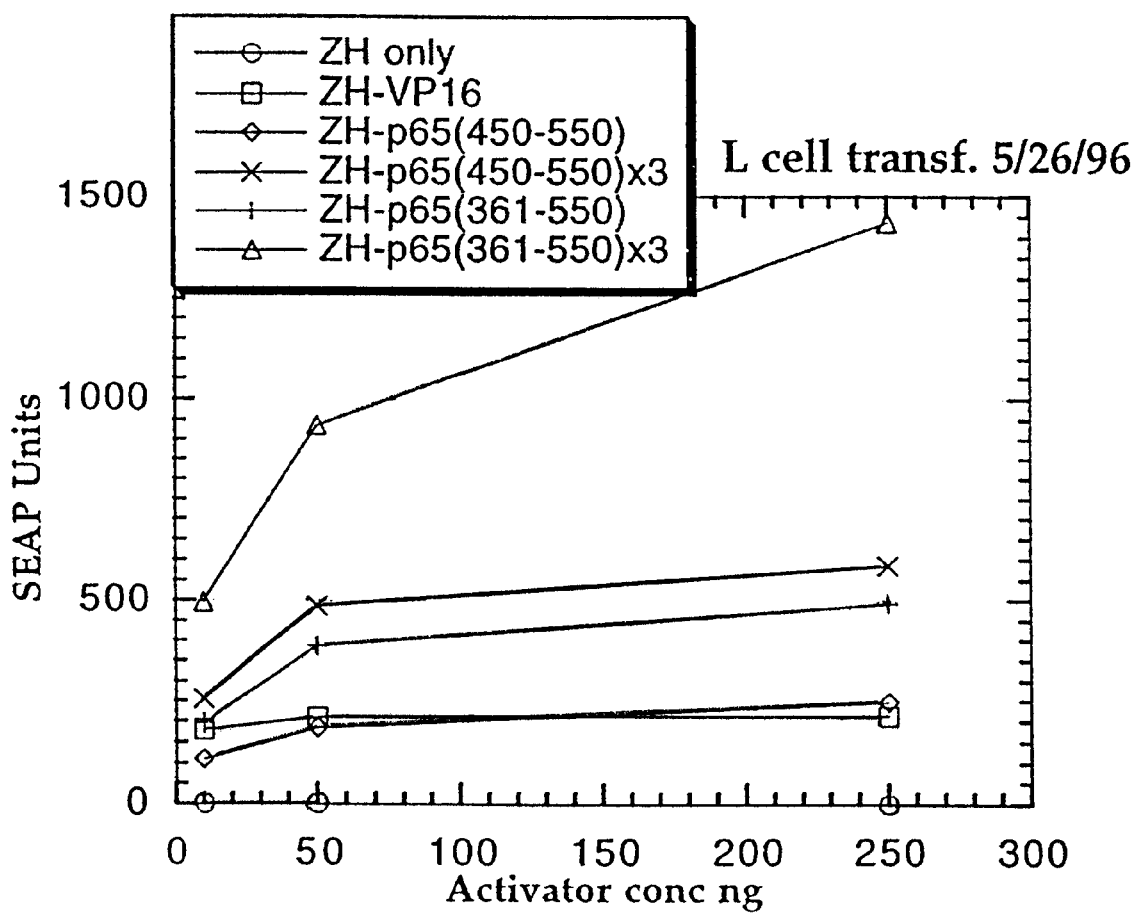
Figure 6:
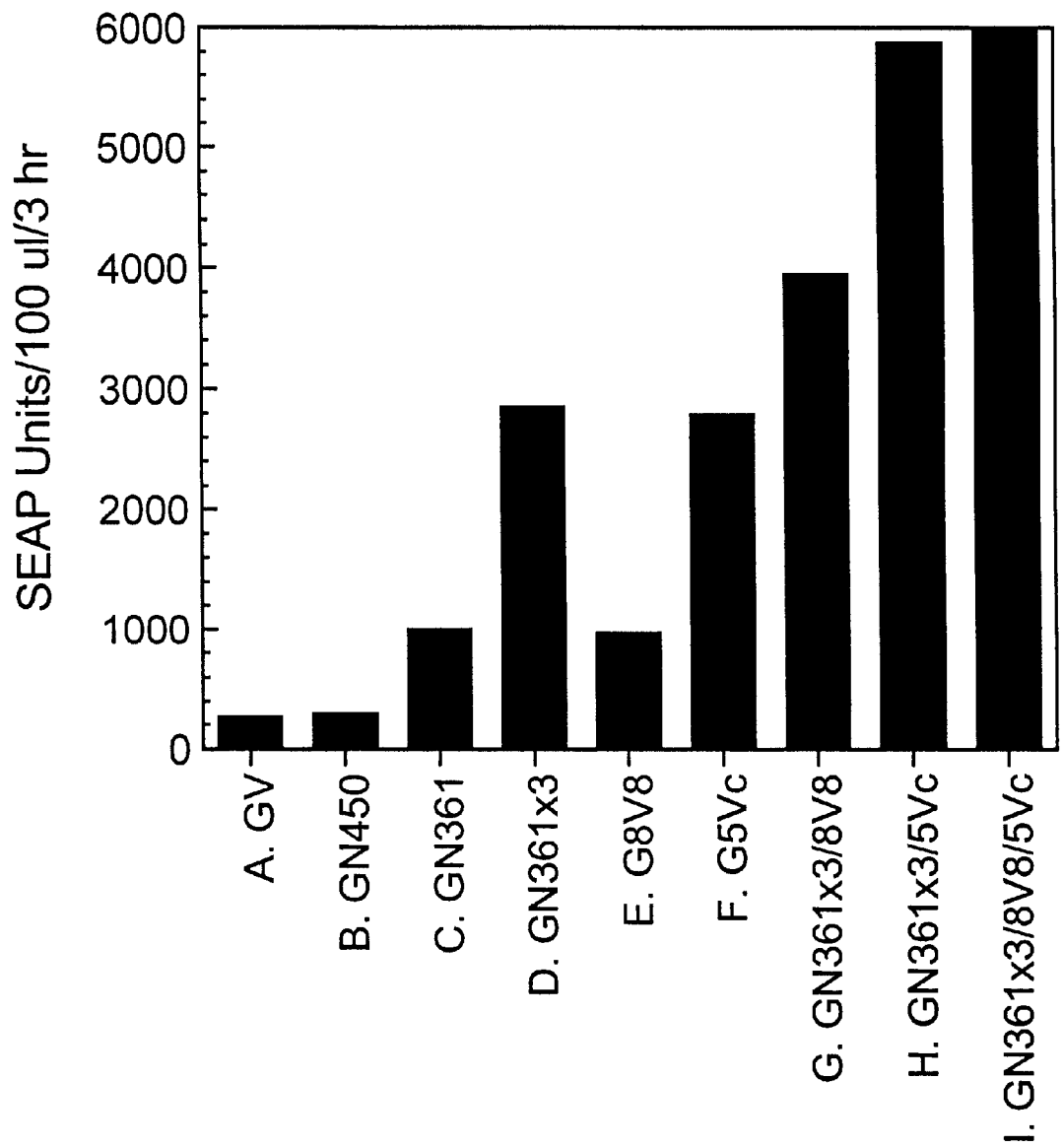

Constructs encoding the following GAL-4-based chimeric transcription factors, among others, were prepared and tested in human cell lines containing stably integrated SEAP reporter constructs containing GAL4 or ZFHD1 recognition sequences, as appropriate:

| chimeric factor | data shown in Figure |
|---|---|
| G-K | FIG. 2 |
| G-KK | |
| G-KKK | |
| G-KKKK | |
| G-KKKKK | |
| G-KKKKKK | |
| G-(V8x2) | FIG. 3 |
| G-(V8x2)₂ | |
| G-(V8x2)₃ | |
| G-(V8x2)₄ | |
| G-(V8x2)₅ | |
| G-(V8x2)₆ | |
| G-D | FIG. 4 |
| G-DD | |
| G-DDD | |
| G-DDDD | |
| G-DDDDD | |
| G-DDDDDD | |
| Z-VP16 | FIG. 5 |
| Z-k | |
| Z-kkk | |
| Z-K | |
| Z-KKK | |
| G-KKK-(V8x2)4 | FIG. 6 |
| G-KKK-DDDDD | |
| G-(V8x2)4-DDDDD | |
| G-KKK-(V8x2)4-DDDDD | |

Figure 7:
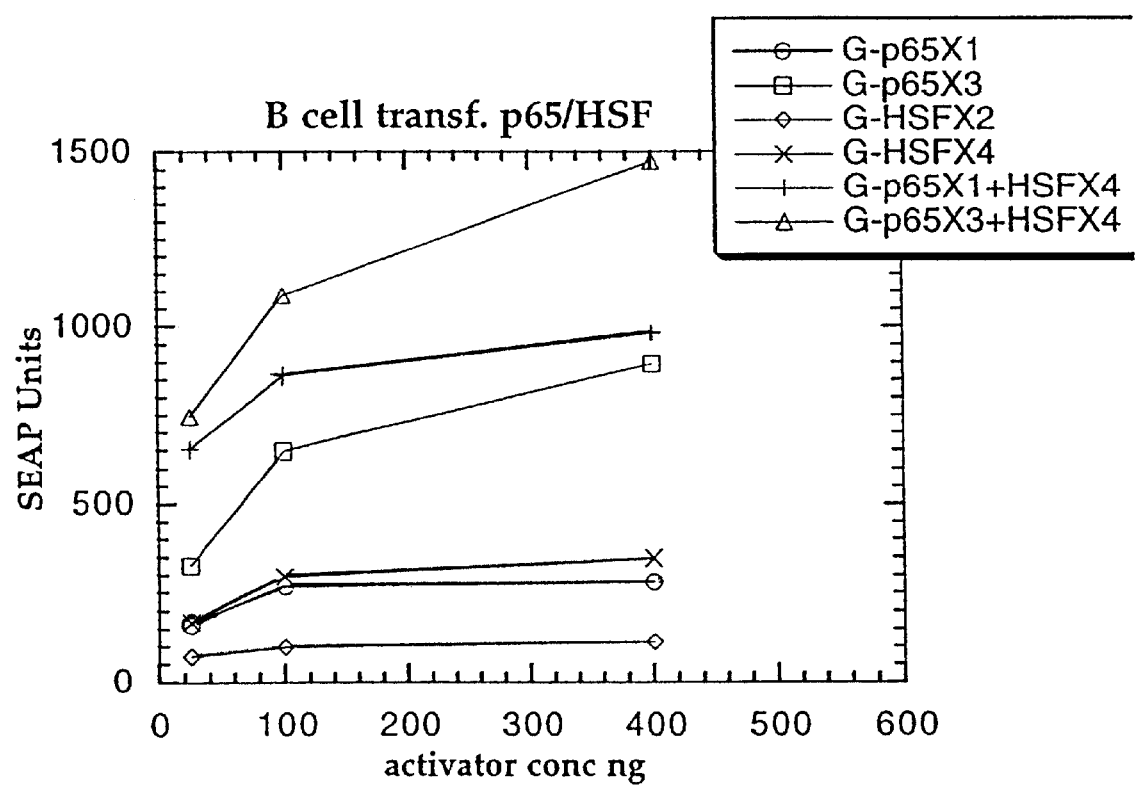

| chimeric factor | data shown in Figure |
|---|---|
| G-K | FIG. 7 |
| G-KKK | |
| G-HSF-HSF | |
| G-HSF-HSF-HSF-HSF | |
| G-K-HSF-HSF-HSF-HSF | |
| G-KKK-HSF-HSF-HSF-HSF | | abbreviations:
G = GAL4 residues 1-94
K = p65(361–550) = "N361" in FIG. 6
k = p65(450–550) = "N450" in FIG. 6
V8x2 = tandem repeat of VP16 V8 sequence with an intervening SerArg resulting from ligation; (V8x2)4 = "8V8" in FIG. 6
D = VP16 C terminal SRDFDLDMLG containing an initial SerArg resulting from ligation = "Vc" in FIG. 6
Z = ZFHD1 ("ZH" in FIG. 5)
HSF = 14 mer (see table below)

Plasmid constructions

PCG-Gal4 vector containing Gal4 DNA binding domain coding sequences between amino acids 1–94 was digested with Xba1 and BamH1. The p65 activation domain sequences between amino acids 361–550 was generated by PCR using the following oligonucleotides:

5'-atgctctagagatgagtttcccaccatggtg-3'[SEQ ID NO:57], and

5'-gcatggatccgctcaactagtggagctgatctgactcag-3'[SEQ ID NO:58].

This fragment was digested with Xba1 and BamH1 and cloned into PCG-Gal4 vector to make PCG-Gal4-p65 (361–550), here after will be referred as PCG-GK. To make PCG-GK2 plasmid, the p65 activation domain containing PCR fragment described above was digested with Xba1 and BamH1 and cloned into Spe1 and BamH1 digested PCG-GK vector. PCG-GK3, 4, 5,6 were all generated following the same approach.

Plasmid PCG-Gal 4 plasmids containing reiterated copies of V8 domain were generated by the following method. The oligonucleotides 5'-ctagagacttcgacttggacatgct-3'[SEQ ID NO:59]; 5'agtccccagcatgtccaagtcgaagtct-3'[SEQ ID NO:60]; 5'-gggggacttcgacttggacatgctgactagttgag-3'[SEQ ID NO:61] and 5'-gatcctcaactagtcagcatgtccaagtcga-3,'[SEQ ID NO:62] were phosphorylated and the first and last pair of oligos were annealed seperately. Together these oligonucleotides make two tandem V8 coding sequences. These annealed oligos were then ligated into Xba1 and BamH1 digested PCG-Gal4 vector. The resulting vector, PCG-GV2 containing two copies of V8 sequences was digested with Spe1 and BamH1. V8x2 oliogos made as described above was cloned into this vector to make PCG-GV4. Same approach was taken to generate PCG-GV6, 8, 10 and 12 plasmids.

PCG-Gal4 plasmids containing reiterated copies of VP16 C-terminus, hereafter refered as D activation domain were constructed as follows. The VP16 C-terminus region was PCR amplified using the following primers:

5'-atgctctagagacggggattccccggggccg-3'[SEQ ID NO:63] and
5'gcatggatcctcattaactagtcccaccgtactcgtcaattcc-3'[SEQ ID NO:64]. The PCR fragments were digested with Xba1 and BamH1 and cloned into PCG-Gal4 vector previously digested with Xba1 and BamH1. The resulting plasmid was designated as PCG-GD. To make PCG-GD2, PCG-GD was digested with Spe1 and BamH1 and ligated with Xba1 and BamH1 digested D fragment described above. PCG-GD3, 4,5 and 6 were constructed using the same approach.

Plasmids PCG-GK3V8 and PCG-GK3D5 were made by digesting PCG-GV8 and PCG-D5 plasmids with Xba1 and BamH1 and cloning the fragments containing V8 and D5 sequences respectively into PCG-GK3 digested with Spe1 and BamH1. Similarly, Xba1 /BamH1 fragment from PCG-GD5 containing D5 sequences was cloned into Spe1/BamH1 digested PCG-GV8 plasmid to construct PCG-V8D5 plasmid. The V8D5 fragment was excised from this plasmid by digesting it with Xba1 and BamH1 and the fragment was cloned into Spe1/BamH1 digested PCG-K3 to make PCG-K3V8D5 plasmid.

PCGNN-ZFHD-p65(450–550) and PCGNN-ZFHD-p65 (361–550) are described above. PCGNN-p65(450–550)x3 and PCGNN-ZFHD-p65(361–550) were made as follows: PCG-Gal4-p65(450–550)x3 and PCG-Gal4-p65(361–550) were digested with Xba1 and BamH1 and the p65 (450–550)x3 and p65(361–550) were excised. These fragments were cloned into Spe1/BamH1 digested PCGNN-ZFHD to generate PCGNN-ZFHD-p65(450–550) and PCGNN-ZFHD-p56(361–550).

PCG-Gal4-HSFX2 containing two copies of HSF14 activation domain was made by phosphorylating and ligating the following oligonucleotides to Xba1 and BamH1 digested PCG-Gal4 plasmid:

5'-ctagagacaccagtgccctgctggacctgttcagcccctcg-3'[SEQ ID NO:65],
5'-ggtcaccgaggggctgaacaggtccagcagggcactggtgtct-3'[SEQ ID NO:66],
5'-gtgaccgtgcccgacatgagcctgcctgaccttgacagcag-3'[SEQ ID NO:67] and
5'-gtgaccgtgcccgacatgagcctgcctgaccttgacagcag-3'[SEQ ID NO:68].

Two additional copies of HSF activation domain were added to Spe1/BamH1 digested PCG-Gal4-HSFX2 plasmid by the same method to generate PCG-Gal4-HSFX4 plasmid. A fragment containing four copies of HSF14 activation domain was excised from PCG-Gal4-HSFX4 by Xba1 and BamH1 digestion. The resulting fragment was cloned into Spe1 and BamH1 digested PCG-Gal4KX1 and PCG-Gal4KX3 to to make PCG-Gal4-K+HSFX4 or PCG-Gal4-K3+HSFX4 plasmids.

reporter Cell Lines

Human 1080 cells were engineered by the stable introduction of a secreted alkaline phosphatatse (SEAP) target gene construct. The target gene construct contained a gene encoding SEAP operably linked to a transcription control sequence containing five copies of a DNA recognitions sequence for GAL4 and a minimal IL-2 promoter. The resultant cells may be used in experiments such as described in Example 3 in which the cells are further transfected with DNA constructs encoding various transcription factors containing one or more DNA binding domains recognized by the target gene construct.

Plasmid Constructions: pLH-G5-IL2-SEAP (as previously described)

Cell Culture: HT1080 cells (ATCC CCL-121), derived from a human fibrosarcoma, were grown in MEM supplemented with non-essential amino acids and 10% Fetal Bovine Serum. Helper-free retroviruses containing the 5xGAL4-IL2-SEAP reporter gene were generated by transient co-transfection of 293T cells (Pear, W. S., Nolan, G. P., Scott, M. L. & Baltimore, D. Production of high-titer helper-free retroviruses by transient transfection. *Proc. Natl. Acad. Sci. USA* 90, 8392–8396 (1993) with a Psi(−) amphotropic packaging vector and the retroviral vector pLH-5× GAL4-IL2-SEAP. To generate a clonal cell line containing the SEAP reporter gene stably integrated, HT1080 cells infected with retroviral stock were diluted and selected in the presence of 300 mg/ml Hygromycin B. Individual clones were screened for the presence of integrated reporter gene by transient transfection of a plasmid encoding a chimeric transcription factor containing a GAL4 DNA binding domain. The most responsive clone, HT1080B, was used for subsequent analysis.

Analysis of Chimeric Transcription Factors

Transfection: HT1080 B cells were grown in MEM supplemented with 10% Bovine Calf Serum. Approximately 2×105 cells/well in a 12 well plate were transiently transfected by Lipofectamine procedure as recommended by GIBCO, BRL. The DNA:Lipofectamine ratio used correspond to 1:6. Cells in each well recieved indicated amounts of effector plasmids and total DNA concentration in each well was adjusted to 1.25 ug with PUC118 DNA. Following transfection, 1 ml fresh media was added to each well. After 24 hrs, 100 ul of the media was assayed for SEAP activity as described.

Representative results:

| chimeric transcription factor | number of activation domains | transcription activation (IL2 promoter) |
| --- | --- | --- |
| GAL4-p65 (361–550) | 1 to 6 | ++++ |
| GAL4-p65 (450–550) | 1 to 6 | +++ |
| GAL4-p65 (361–450) | 1 to 6 | -- |
| GAL4-K13 (SRDFADMDFDALL [SEQ ID NO: 69] derived from p65) | 1 to 6 | +++ |
| GAL4-Oct2 Q domain (aa 95–160) | 1 to 6 | -- |
| GAL4-Oct2 P domain (aa 438–479) | 1 to 6 | -- |
| GAL4-HSF (aa 409–444) | 1 to 4 | +++ |
| GAL4-HSF14 (DLDSSLASIQELLS) [SEQ ID NO: 70] | 1 to 4 | ++ |
| GAL4-EWS11 (SRSYGQQGSGS) [SEQ ID NO: 71] | 1 to 8 | -- |
| GAL4-V8x2 (DFDLDMLGDFDLDMLGSR) [SEQ ID NO: 72] | 1 to 12 | ++ |
| GAL4-D (VP16 aa 459–490) | 1 to 6 | +++ |
| GAL4-VP16 (VP16 aa 411–490) | 1 to 4 | ++ |

What is claimed is:

1. A recombinant DNA sequence encoding a chimeric transcription factor comprising (a) one or more copies of a peptide sequence comprising all or part of a peptide sequence spanning positions 361 through 550 of human NF-κB p65, or a peptide sequence derived therefrom, and (b) a peptide sequence heterologous thereto and which is selected from a peptide sequence within the sequence of VP16 B, VP16 C, HSF, or CTF.

2. A cell comprising the recombinant DNA sequence of claim 1.

* * * * *